(12) United States Patent
Tamura

(10) Patent No.: US 6,599,248 B1
(45) Date of Patent: Jul. 29, 2003

(54) METHOD AND APPARATUS FOR ULTRASOUND DIAGNOSTIC IMAGING

(75) Inventor: Tadashi Tamura, North Haven, CT (US)

(73) Assignee: Aloka, Wallingford, CT (US)

( * ) Notice: Subject to any disclaimer, the term of this patent is extended or adjusted under 35 U.S.C. 154(b) by 59 days.

(21) Appl. No.: 09/757,422

(22) Filed: Mar. 20, 2001

(51) Int. Cl.⁷ .................................................. A61B 8/00
(52) U.S. Cl. ..................................................... 600/454
(58) Field of Search ............................... 600/443, 447, 600/454, 455, 444, 456, 448; 128/516

(56) References Cited

U.S. PATENT DOCUMENTS

| | | | |
|---|---|---|---|
| 5,513,640 A | * | 5/1996 | Yamazaki et al. .......... 600/443 |
| 5,653,234 A | | 8/1997 | Kim et al. |
| 5,980,459 A | * | 11/1999 | Chiao et al. ................ 600/447 |
| 6,012,458 A | | 1/2000 | Mo et al. |
| 6,050,947 A | * | 4/2000 | Rhyne et al. ............... 600/447 |
| 6,123,670 A | * | 9/2000 | Mo ............................ 600/447 |
| 6,126,603 A | * | 10/2000 | Hatfield et al. ............. 600/454 |

* cited by examiner

Primary Examiner—Francis J. Jaworski
Assistant Examiner—Maulin Patel
(74) Attorney, Agent, or Firm—Bachman & LaPointe, P.C.

(57) ABSTRACT

A method and apparatus of blood flow imaging is disclosed. The method comprises receiving a beamformed signal indicative of an ultrasound signal reflected from a target within a body, based upon the beamformed signal, imaging tissue within the body, generating thereby a tissue signal, based upon the beamformed signal, detecting blood flow within the body, generating thereby a blood flow signal and combining the tissue signal and the blood flow signal generating thereby a composite image of tissue and blood flow.

53 Claims, 19 Drawing Sheets

Block Diagram of Ultrasound Imaging System

Block Diagram of Ultrasound Imaging System

US 6,599,248 B1

METHOD AND APPARATUS FOR ULTRASOUND DIAGNOSTIC IMAGING

FIELD OF THE INVENTION

The present invention relates to the field of medical ultrasound imaging, especially blood flow imaging in living organisms.

BACKGROUND OF THE INVENTION

An ultrasound imaging system scans a human body with ultrasound beams to create two-dimensional images of organs such as the heart, a fetus, the liver, or sometimes blood vessels (e.g. carotid arteries). This ultrasound image mode is called a B-mode image, which is a grayscale image. In addition to the B-mode image, today's high performance ultrasound imaging systems can detect and display blood flow. Because blood flow provides important physiological information to clinicians, it is desirable to display blood flow and its physiological state. Blood flow is usually displayed as a color image on top of the grayscale image (or B-mode) of vessel structures, such as vessel walls, bifurcations, or sometimes lesions. This mode is usually called color flow or color Doppler if the blood detection involves the Doppler technique. More quantitative measurements of blood flow are usually performed with the spectral pulsed-wave (PW) Doppler.

The sound pressure level of an ultrasound signal scattered from blood is much lower (usually −20 to −40 dB lower) than that scattered from tissue. Therefore, the signal-to-noise ratio (SNR) in an ultrasound signal is critical where color flow or color Doppler detection is used. Because SNR is critical in color flow and color Doppler detection, many efforts have been made to increase the signal to noise ratio in the ultrasound signal and to increase sensitivity in detecting blood flow. One such method is to use a narrower band ultrasound signal for color flow or color Doppler detection than that used for tissue detection. An additional integrator in the axial direction may also be used to further increase the SNR. Unfortunately, reducing the bandwidth of the ultrasound signal and increasing the number of integrators in the axial direction will both limit spatial (or axial) resolution substantially. As a result of these methods, color flow and color Doppler imaging have several times lower spatial resolution than B-mode tissue imaging does. For certain applications, such as the early detection of certain vascular diseases, the reduced spatial resolution associated with color flow and color Doppler imaging is not ideal. In addition, since blood flow is usually displayed in colors rather than grayscale, the blood flow image is usually superimposed on the grayscale image of blood vessel walls. Unfortunately, the blood flow image often overwrites the image of the vessel walls, making the borders between vessel walls and blood unclear.

SUMMARY OF THE INVENTION

A method and apparatus of blood flow imaging is disclosed. The method comprises receiving a beamformed signal indicative of an ultrasound signal reflected from a target within a body. Based upon the beamformed signal, imaging tissue within the body is performed, generating thereby a tissue signal. In addition, based upon the beamformed signal, detecting blood flow within the body is performed, generating thereby a blood flow signal. The tissue signal and the blood flow signal are combined to generate a composite image of tissue and blood flow.

BRIEF DESCRIPTION OF THE DRAWINGS

The invention will now be described by way of the drawings in which.

DETAILED DESCRIPTION OF THE INVENTION

Ultrasound Imaging System

Figure 1:
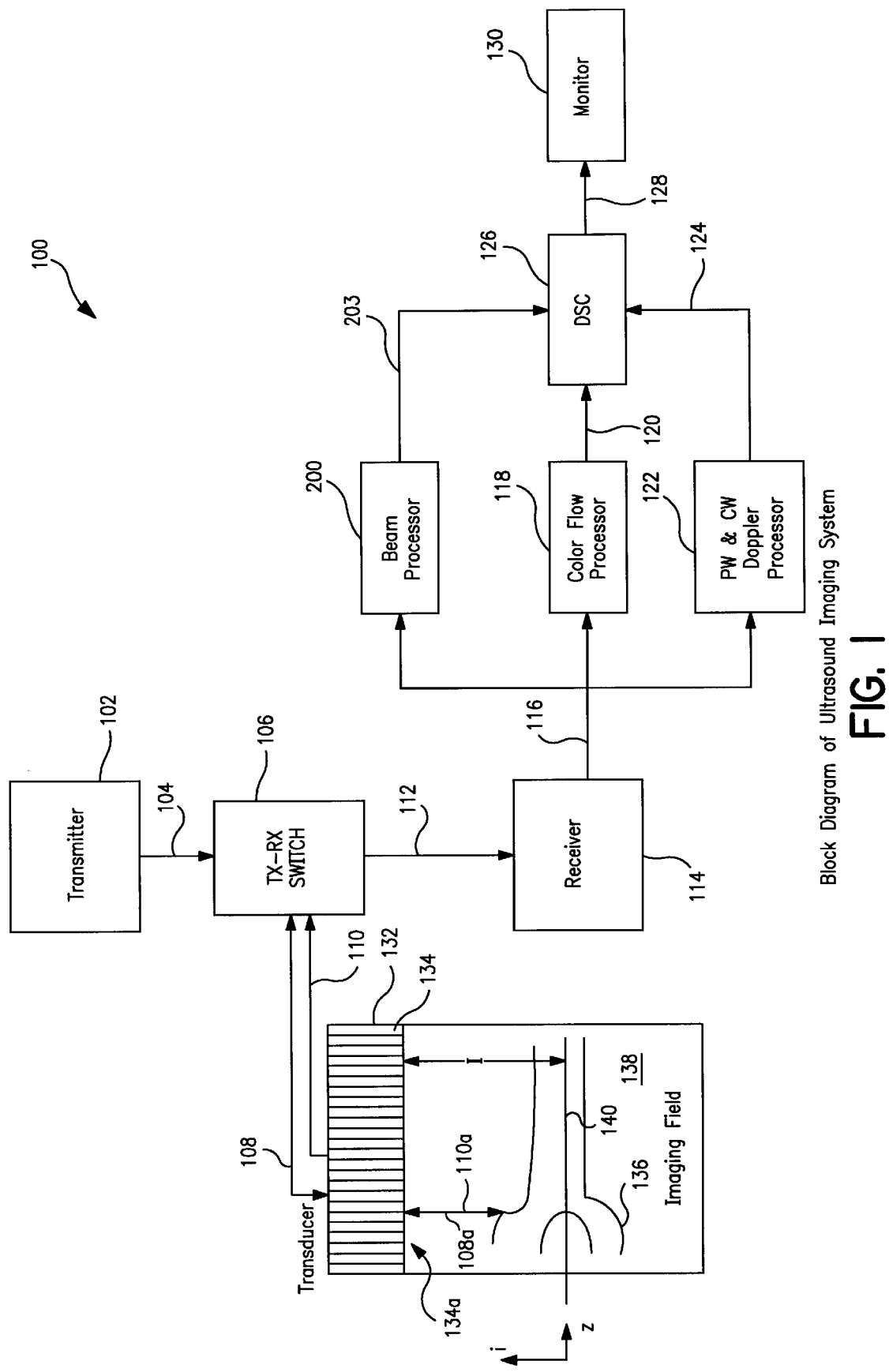
FIG. 1 is a schematic block diagram of an ultrasound imaging system.

FIG. 1 shows a block diagram of an ultrasound imaging system 100, capable of creating B-mode images, color flow images and pulsed wave (PW) and continuous wave (CW) spectral Doppler velocity measurements. The ultrasound imaging system 100 comprises a transmitter 102, a receiver 114, a multiple-element array transducer 132 (or single element transducer), a transmit-receive (TX-RX) switch 106, a beam processor 200, a color flow processor 118, a pulsed wave and continuous wave Doppler processor 122, a digital scan converter (DSC) 126 and a display monitor 130. In addition to these electronic circuits, a timing/clock circuit, a host CPU computer to control the operation of all electronic circuits described above and a power supply are included in the ultrasound imaging system 100 although these parts are not illustrated in FIG. 1.

Radio frequency (RF) electrical signals 104 are generated in the transmitter 102. These signals 104 are sent to the transducer 132 through the TX-RX switch 106 which protects the receiver 114 from the high-voltage RF signals 104. The RF signals 104 are converted to ultrasound wave signals 108a by a plurality of transmit elements 134 in the ultrasound transducer 132. The transmit elements 134 are made of a piezoelectric material. The number of RF signals 104 and ultrasound signals 108a generated therefrom, matches the number of transducer elements 134 in the transmit aperture 134a of the transducer 132. The RF signals 104 are appropriately delayed and formed in such a way that the ultrasound wave-front 140 created by the ultrasound signals 108a is focused at the focal depth, "I," in the imaging field 138. Thus, the short, pulsed ultrasound wave 108a is transmitted and reflected or scattered from targets 136, such as human body organs, in the imaging field 138. Reflected signals 110a, returning from the targets 136, are detected by the plurality of transducer elements 134 and converted back into to electrical signals 110, 112 which are then fed to the receiver 114 through TX-RX switch 106.

In the receiver 114, the electrical signals 112 are subject to signal conditioning such as bandpass filtering, pre-amplification and time-gain control (TGC) compensation. TGC compensates for the attenuation of the ultrasound wave 108a as the depth, of the target 136 within the body increases. The receiver 114 in FIG. 1 also includes a beamformer (not shown) comprising multiple channels for signal processing. Each of such channels comprises an analog to digital (A/D) converter, delay circuits and summing circuits so as to focus and form (i.e. beam form) the ultrasound signal 108a so that the reflected beam 110a is focused and narrow at every depth. Time delays between the ultrasound waves 108a and the reflected waves 110a are determined by the geometrical distance the ultrasound wave 108a must travel to the target 136. Each beamformer channel is connected to corresponding transducer element 134 for a given depth. The beamformer channels may also contain quadrature mixers (not shown) so that baseband (BB) or intermediate frequency (IF) signals are obtained and beamformed at the BB or IF frequency rather than at a radio frequency (RF) signal level. For those skilled in the art, it will be seen that the present invention can be applied to any type of beamformers. The RF beamformer version (for example at 40 MHz) is described herein.

The output of the receiver 114 is a beamformed RF signal 116. The beamformed RF signal 116 is fed to the beam processor 200, the color flow processor 118 and the pulsed wave & continuous wave Doppler processor 122 to obtain the B-mode signal 203, the color flow signal 120 and the Doppler signal 124, respectively. Signals 203, 120, and 124 are fed to the digital scan converter 126 in order to display these signals on the display monitor 130 in a raster-scan format. The transmitted and reflected ultrasound signals 108a, 110a may form an imaging field of linear (rectangle), sector, convex and other formats, depending on the type of transducers. In FIG. 1, a linear (rectangle) image format is displayed as an example.

Figure 2:
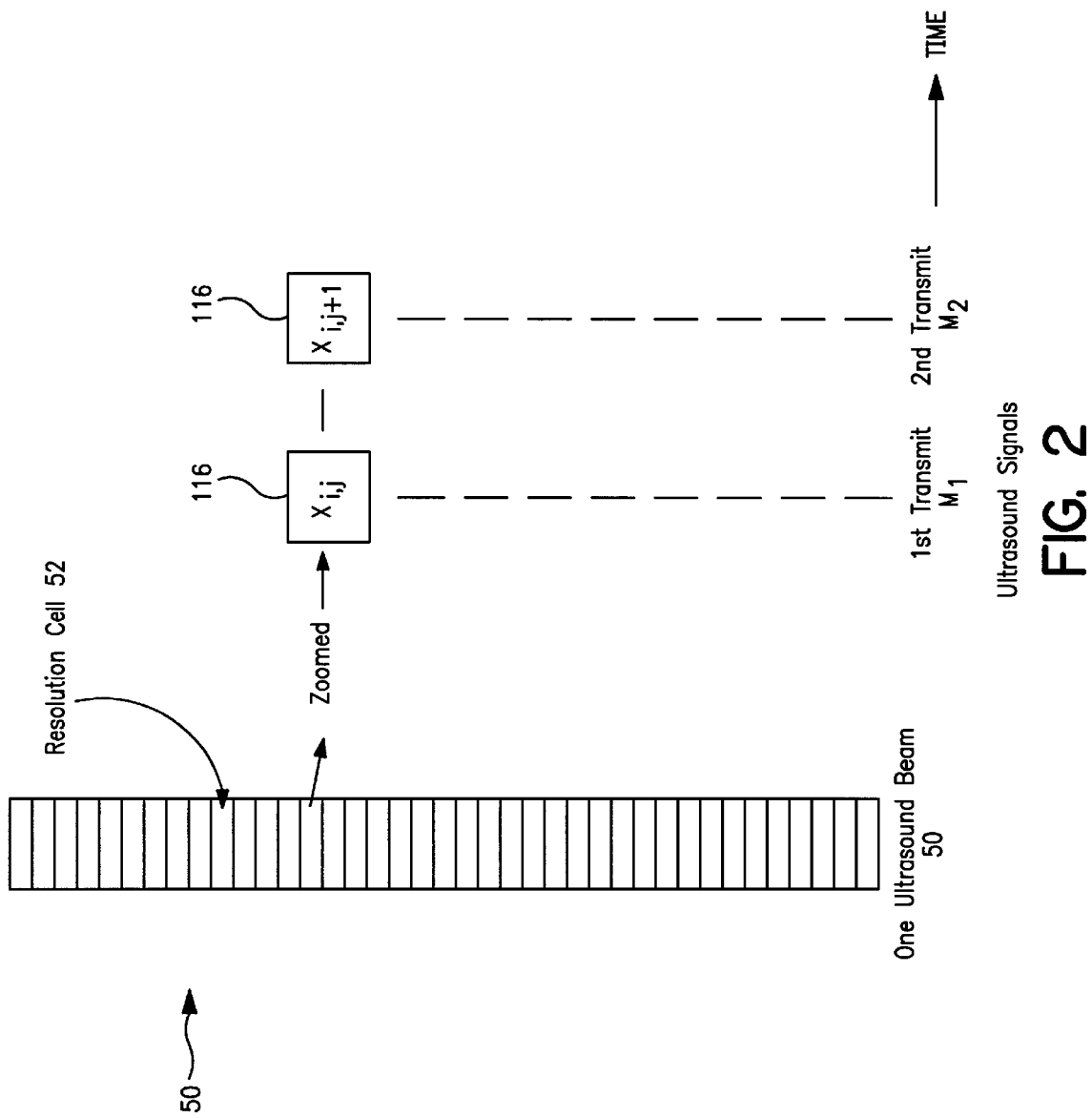
FIG. 2 is a schematic diagram of an ultrasound beam comprising a plurality of resolution cells wherein in one of the resolution cells a beamformed RF signal generated at a second transmission time is subtracted from a beamformed RF signal generated at a previous transmission time.

Referring to FIG. 2, an ultrasound imaging field comprises a plurality of adjacent ultrasound beams 50. One such beam is shown in FIG. 2. The ultrasound beam 50 comprises a plurality of adjacent resolution cells 52 containing the beam formed RF signals 116.

In general, the beam processor 200 processes the beamformed RF signal 116 in order to obtain a B-mode signal 203 representing tissue in the imaging field 138. This processing may involve amplitude (or envelope) detection by quadrature detection or Hilbert-transforming, low-pass filtering, log-compression, and anti-aliasing filtering as is known in the art. Alternatively, partially processed signals in the beam processor 200, for example, the quadrature detected signals, can be provided to the color flow processor 118. In the present invention, a method and apparatus for blood flow detection is added to the beam processor 200 as seen in FIG. 4A.

Figure 3:
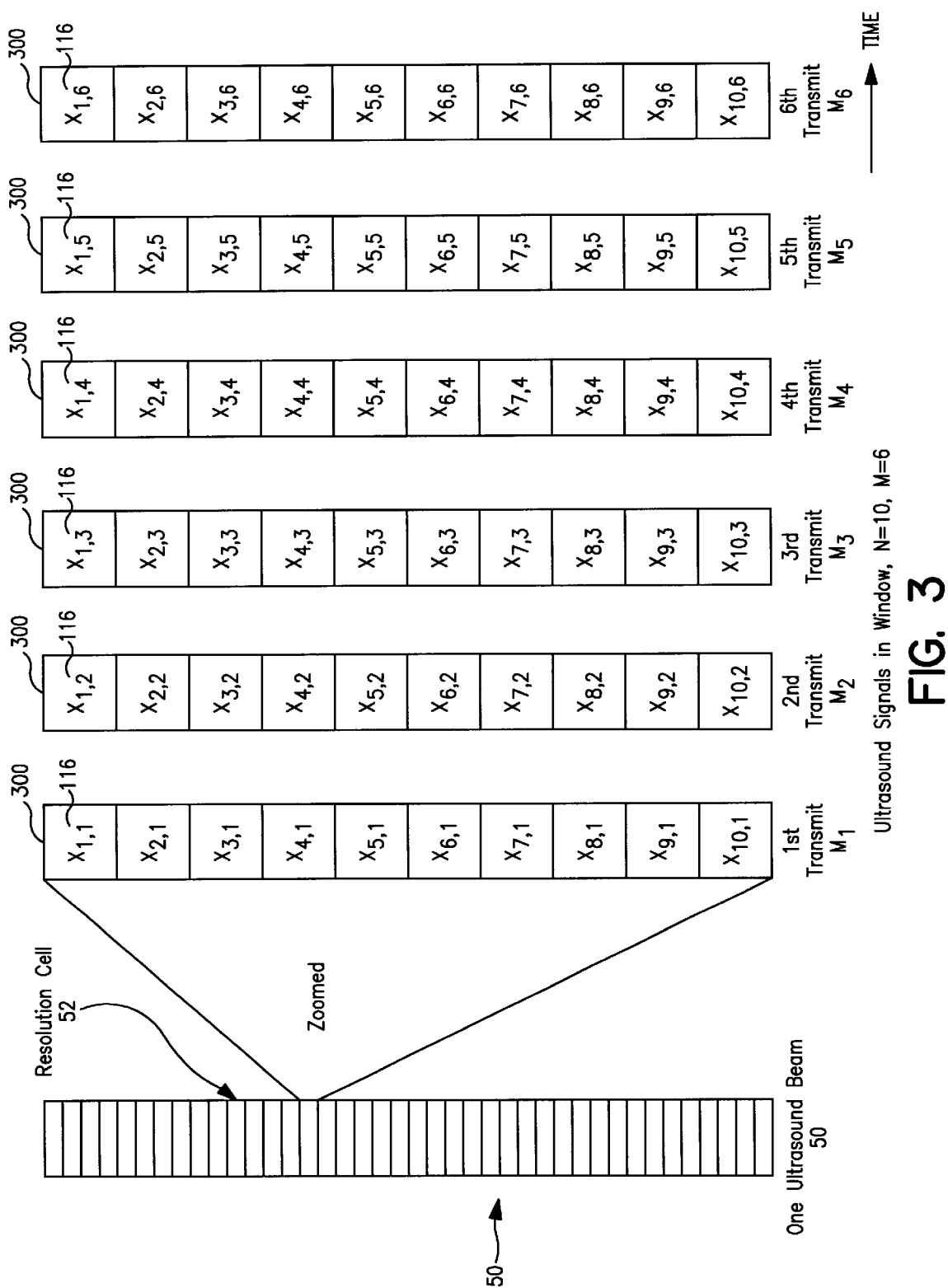
FIG. 3 is a schematic diagram of the ultrasound beam of FIG. 2 showing a resolution cell expanded to show a plurality of windows therein at subsequent transmission times including a plurality of beamformed RF signals.

FIG. 3 shows ultrasound beam 50 including a plurality of resolution cells 52. Each resolution cell 52 includes an axial window 300 of predetermined length, N. As best understood from FIG. 3, the axial window 300, over successive time intervals, M, includes a plurality of beamformed RF signals 116 received at M different times (e.g., two different transmit/receive sequences) in one direction at the same focal point. As in FIG. 2, each beamformed RF signal 116 is depicted as $X_{ij}$, where i=1, 2, 3, ... N is the depth index of the signal 116 within the resolution cell 52 of the ultrasound beam 50, and j=1, 2, 3, ... M is the time step at which the signal 116 is transmitted. In FIG. 3, the number, N, i.e., the number of beamformed RF signals 116 in the axial windows 300 is set at ten. However, it will be recognized that this number can be increased or decreased. Similarly, the number, M, i.e., the number of beamformed RF signals 116 transmitted, can vary from two to several, but is set at six in FIG. 3 as an example. All ten signals 116 can be used or only a few or one can be used to represent a particular window 300 at a specific time "j". The higher N, the greater the amount of data available in axial averaging, resulting in higher SNR. By employing various methods to one or more beamformed RF signals 116 within the windows 300, the SNR for each resolution cell 52 in beam 50 can be increased. These various methods are described in further detail hereinbelow.

Figure 4A:
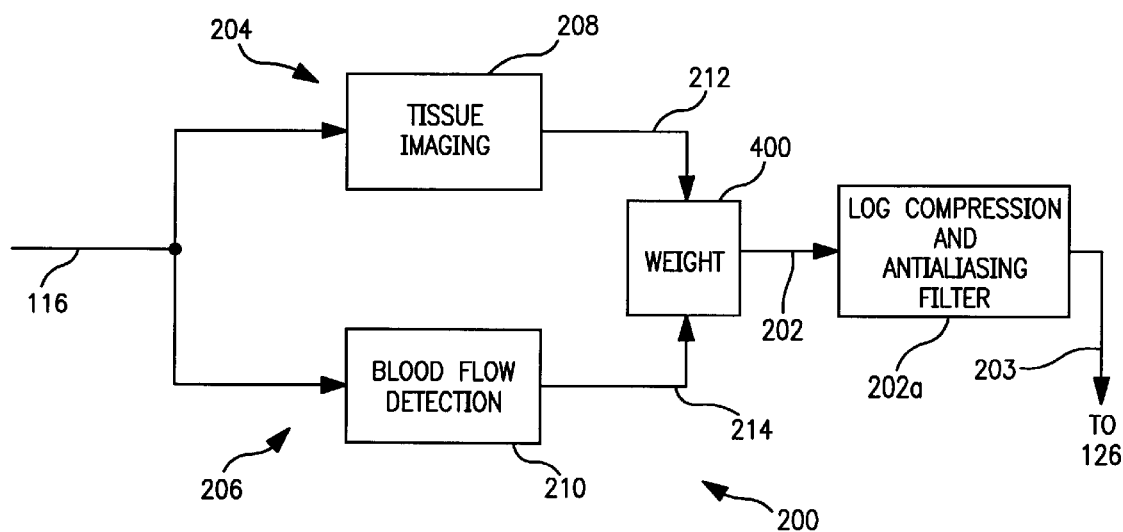
FIG. 4A is a schematic block diagram of an ultrasound beam processor including a tissue imaging system, a blood flow detection system and a weight coefficient generator.

Referring to FIG. 4A, in the beam processor 200, a series, $X_{ij}$, of beamformed RF signals 116 originating within a window 300 at a first time, for example $M_1$, is provided to a first signal branch 204 and a second signal branch 206 of the beam processor 200. The first signal branch 204 of the beam processor 200 comprises a tissue imaging system 208 operative to accept as input thereto the beamformed RF signals 116 and to provide as output a tissue image signal 212. The tissue imaging system 208 comprises a tissue image detection device 216 (FIG. 4B) in signal communication with a synchronizing device such as a resampling device 220. A tissue image signal 218 is provided as input to the resampling device 220. The resampling device 220 provides as output a resampled tissue signal 212 to a weight coefficient generator 400. The second signal branch 206 of the beam processor 200 comprises a blood flow detection system 210 operative to accept as input thereto the beamformed RF signals 116 and to provide as output a blood flow signal 214 to the weight coefficient generator 400. The weight coefficient generator 400 applies weight coefficients to the amplitudes of the resampled tissue image signal 212 and to the blood flow signal 214, and provides as output 202 a weighted sum of the resampled tissue image signal 212 and the blood flow signal 214. This is a composite image 202 of tissue and blood flow and is made available for further processing, e.g., log-compression and anti-aliasing filtering at 202a and thence to the digital scan converter 126.

RF Subtraction

Flowing blood can generally be distinguished from stationary tissue by analyzing the difference between two successive beamformed RF signals 116. The two successive beamformed RF signals 116 are part of successive transmit/receive sequences originating at the transmitter 102, proceeding to the transducer 132, the target 136 and received at the receiver 114. Two successive ultrasound signals 108a are directed in substantially the same direction from the transducer 132 and at substantially the same focal point in the imaging field 138. As noted hereinabove, this method is described using the beamformed RF signals 116 (at about 40 MHz), but the same method can be applied where the receiver 114 performs beamforming in either the baseband (BB) frequency or the intermediate frequency (IF) as well. In particular, a first ultrasound signal 108a, $x_{i,j}$, is launched at a target 136 at time j, and a second ultrasound signal, 108a, $x_{i,j+1}$, is launched at the target at time j+1. If the difference between the two signals, as represented by the subsequent beamformed RF signals 116, $X_{i,j}$, $X_{i,j+1}$, is zero, then $X_{i,j+1}=X_{i,j}$ and the target is stationary. If the difference between the two signals is nonzero, then there has been some change in the position of the target. FIG. 2 conceptually illustrates this method of blood flow detection. Each beam 50 comprises a plurality of image resolution cells 52, and each resolution cell 52 is the difference between the beamformed RF signals $X_{ij}$ and $X_{ij+1}$. The output of the cells is $$\text{Output} = X_{i,j} - X_{i,j+1} \qquad (1)$$

where i denotes the depth index in the axial direction (i.e., along the beam 50) and j denotes the $j^{th}$ beamformed RF signal 116.

As noted previously, the sound pressure level of an ultrasound signal scattered from blood is very small and is usually much lower (usually −20 to −40 dB lower) than that scattered from tissue. Therefore, the difference between RF signals $X_{ij}$ and $X_{ij+1}$, where these signals indicate blood flow and are subject to random electronic noise conditions, will be very small and thus the signal to noise ratio (SNR) of the resolution cell 50 will be small. To make use of the difference between beamformed RF signals $X_{ij}$ and $X_{ij+1}$, it is desirable to increase the SNR of the beamformed RF signals $X_{ij}$ and $X_{ij+1}$ by the methods described hereinbelow.

By increasing the number of ultrasound signals 108a transmitted and thus the number of beamformed RF signals 116 processed, the SNR in each resolution cell 52 can be increased. The receiver 114 provides as output beamformed RF signals, $X_{ij}$, 116 at a rate of, for example, 40 Mhz. However, a typical display monitor 130 can only display on the order of 400 to 500 samples per beam 50. Therefore, for each resolution cell 52 of the ultrasound beam 50 that the monitor 130 can display, the receiver 114 can generate several thousand beamformed RF signals 116. Thus, the beam processor 200 has numerous beamformed RF signals 116 available for each resolution cell 52 of the ultrasound beam 50, and the number of beamformed RF signals 116 per resolution cell 52 can be increased, as shown in FIG. 3.

Sum-of-Absolute-Differences

By expanding the beamformed RF signals 116 in the window 300, a sum-of-absolute-differences (SAD) method can be used to increase the SNR of each of the resolution cells 52. The sum-of-absolute-differences is a method of analyzing the difference between a reference signal (or set of data) and a delayed or displaced version of the reference signal (or set of data). The method of the sum-of-absolute-differences for each resolution cell 52 of ultrasound beam 50 is generally expressed as follows:

$$SAD = \sum_{i=1}^{N} |X_{i,j} - X_{i,j+1}| \qquad (2)$$

where i is the depth index of the beamformed RF signal 116 in the axial direction (i.e., along the beam 50) and j is the time of the $j^{th}$ transmission. Utilizing two successive transmissions of the beamformed RF signal 116, the SAD of Eqn. (2) can be implemented by the beam processor 200 as shown in FIG. 4C.

Figure 4B:
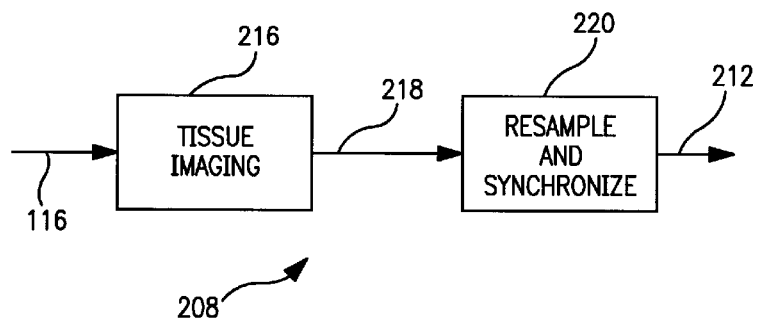
FIG. 4B is a schematic block diagram of a tissue imaging system including a tissue imaging detection device and a synchronizing device.
Figure 4C:
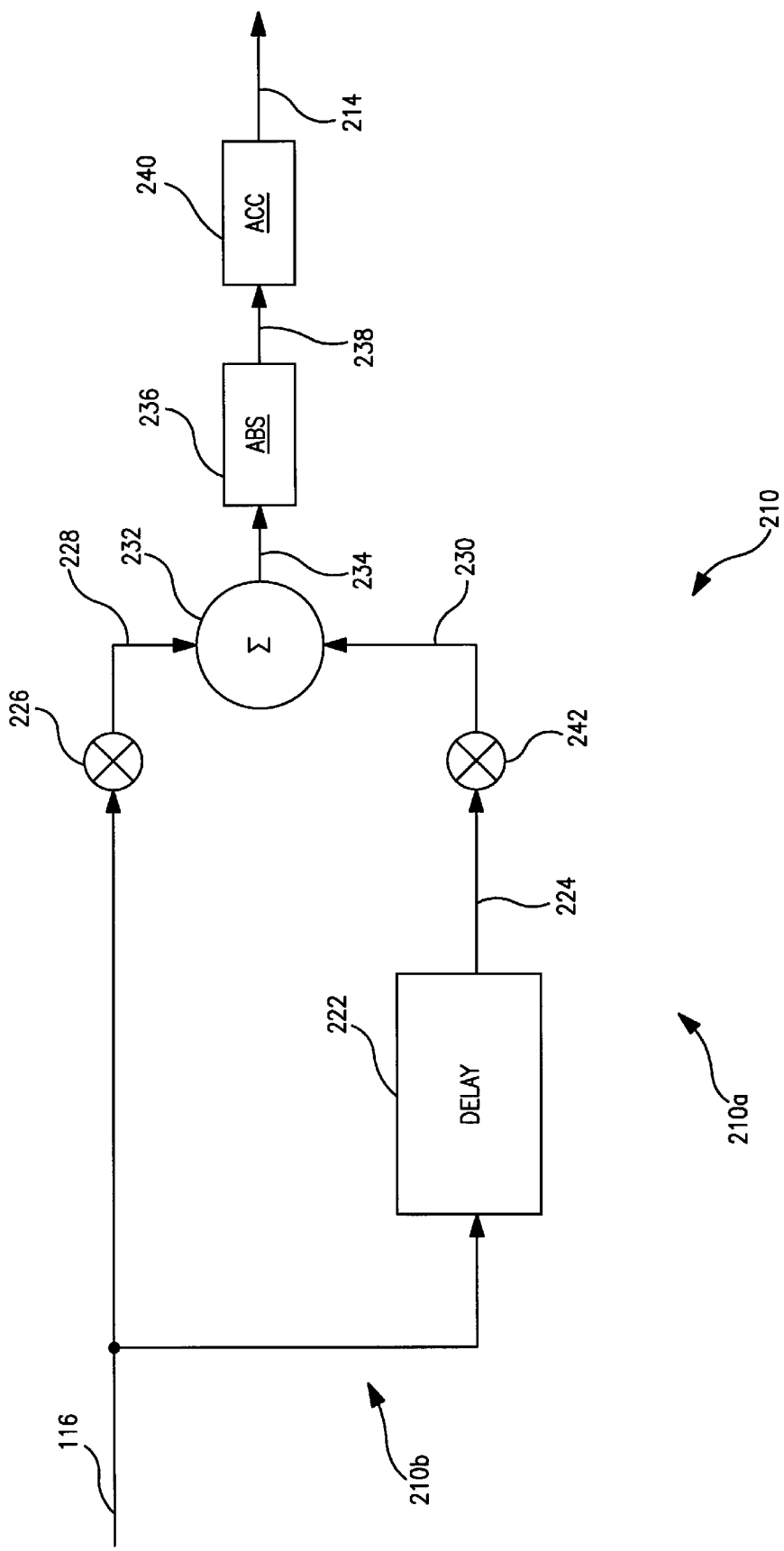
FIG. 4C is a schematic block diagram of a sum-of-absolute-difference function generator.

In FIG. 4C, the blood flow detection system 210 comprises a SAD analyzer 210a. The SAD analyzer 210a comprises a first order finite-impulse-response (FIR) filter 210b, an absolute value generating device 236 and an accumulator 240. A series of beamformed RF signals, $X_{i,j}$, 116 originating at time "j" within window 300 are stored in a line buffer 222 of the FIR filter 210b until a second series of beamformed RF signals, $X_{i,j+1}$, 116 originating at time "j+1" is applied to the FIR filter 210b. Multiplier 226 receives the beamformed RF signal 116 ($X_{i,j+1}$) and multiplies that signal by a fixed coefficient of −1. Multiplier 242 receives the delayed beamformed RF signal 116 ($X_{i,j}$) from the line buffer 222 and multiplies that signal by a fixed coefficient of 1. The multiplied signals 228, 230 are then provided to an adder 232, which sums the multiplied signals 228, 230. The output 234 of FIR filter 210b is the difference between the initial and delayed beamformed RF signals 116 (i.e., $X_{i,j}-X_{i,j+1}$). The difference 234 is then provided to an absolute value generating device 236 that calculates the absolute value of the difference (i.e., $|X_{i,j}-X_{i,j+1}|$). The absolute value of the difference 238 is then provided to the accumulator 240, which determines the window 300 size "N" (i.e. the number of beamformed RF signals 116 in each transmission) and sums N absolute values thereof $$\sum_{i=1}^{N} |X_{i,j} - X_{i,j+1}|$$

to create the SAD blood flow signal 214 for a single resolution cell 52. The output 214 of the SAD analyzer 210a is provided as input to the weight coefficient generator 400.

In FIG. 4B, because of the fact that the SAD blood flow signal 214 for each resolution cell 52 is generated using two transmissions of the beamformed RF signal 116 and the tissue imaging signal 212 for each resolution cell 52 would normally be generated using one beamformed RF signal 116, the number of blood flow signals 214 provided as output by accumulator 240 is less than, or not synchronized with, the number of tissue imaging signals 212 provided as output by tissue detection device 216. Therefore, a synchronizer, such as a resampling device 220, is included in the first signal branch 204 to synchronize or decrease the number of the tissue signals 218 so that the number of tissue signals 218 matches or is synchronized with the number of blood flow signals 214 provided as output by accumulator 240, thus synchronizing the beamformed signal 116 with a displaced or delayed version thereof. The resampling device 220 provides as input to the weight coefficient generator 400 the resampled tissue signal 212.

Figure 9:
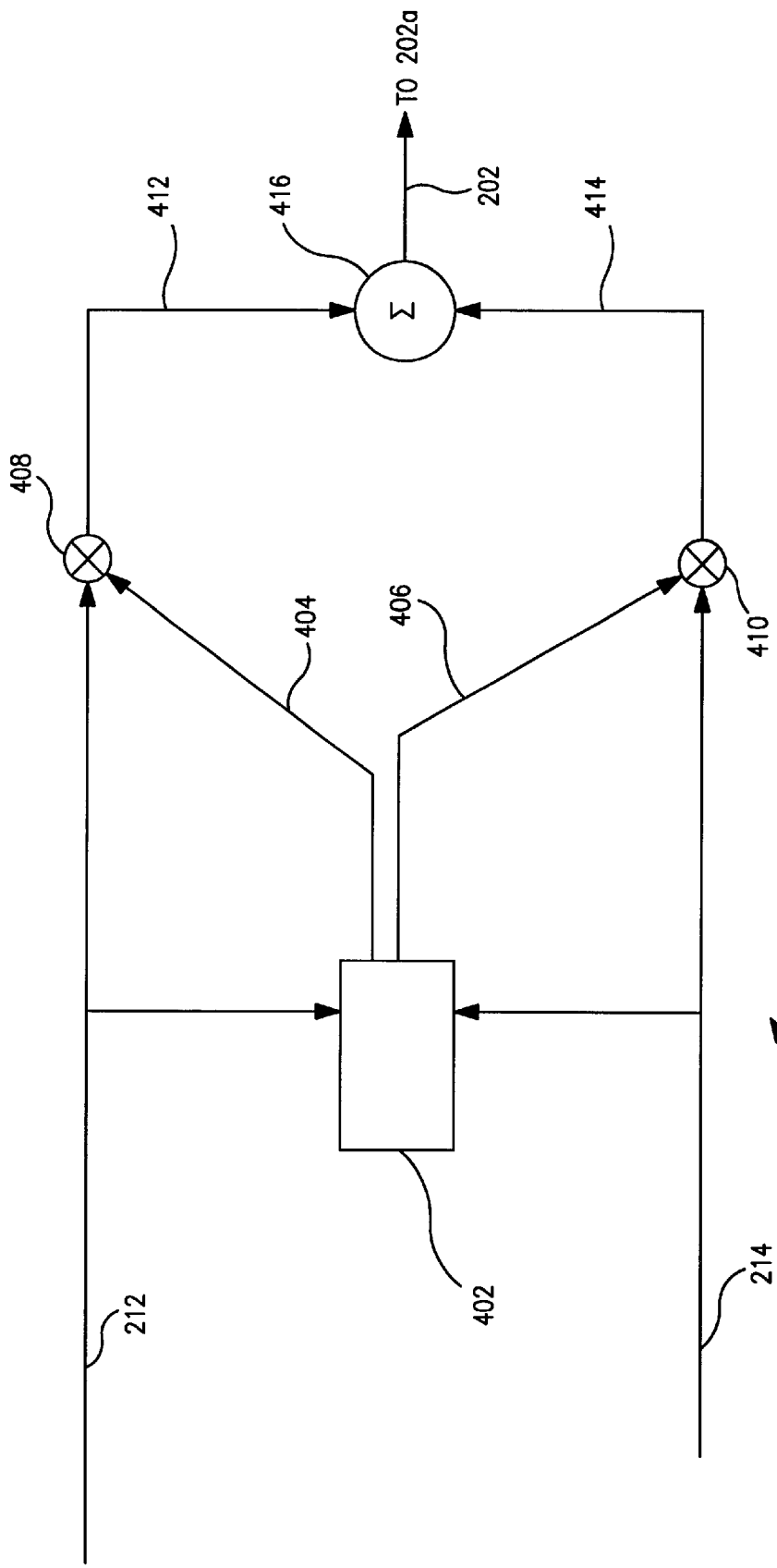
FIG. 9 is a first schematic block diagram of the weight coefficient generator of FIG. 4A.
Figure 10:
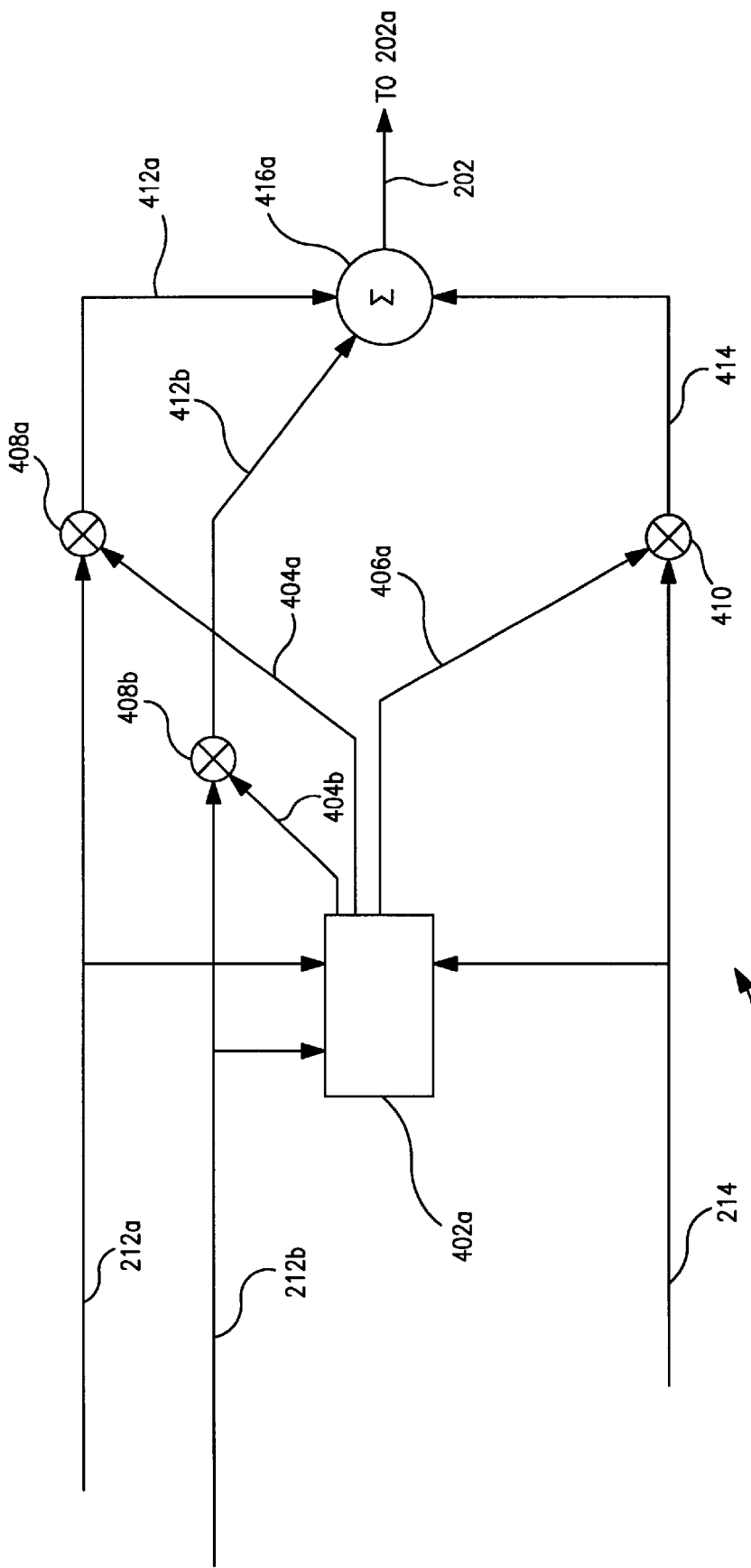
FIG. 10 is a second schematic block diagram of the weight coefficient generator of FIG. 4A.
Figure 11:
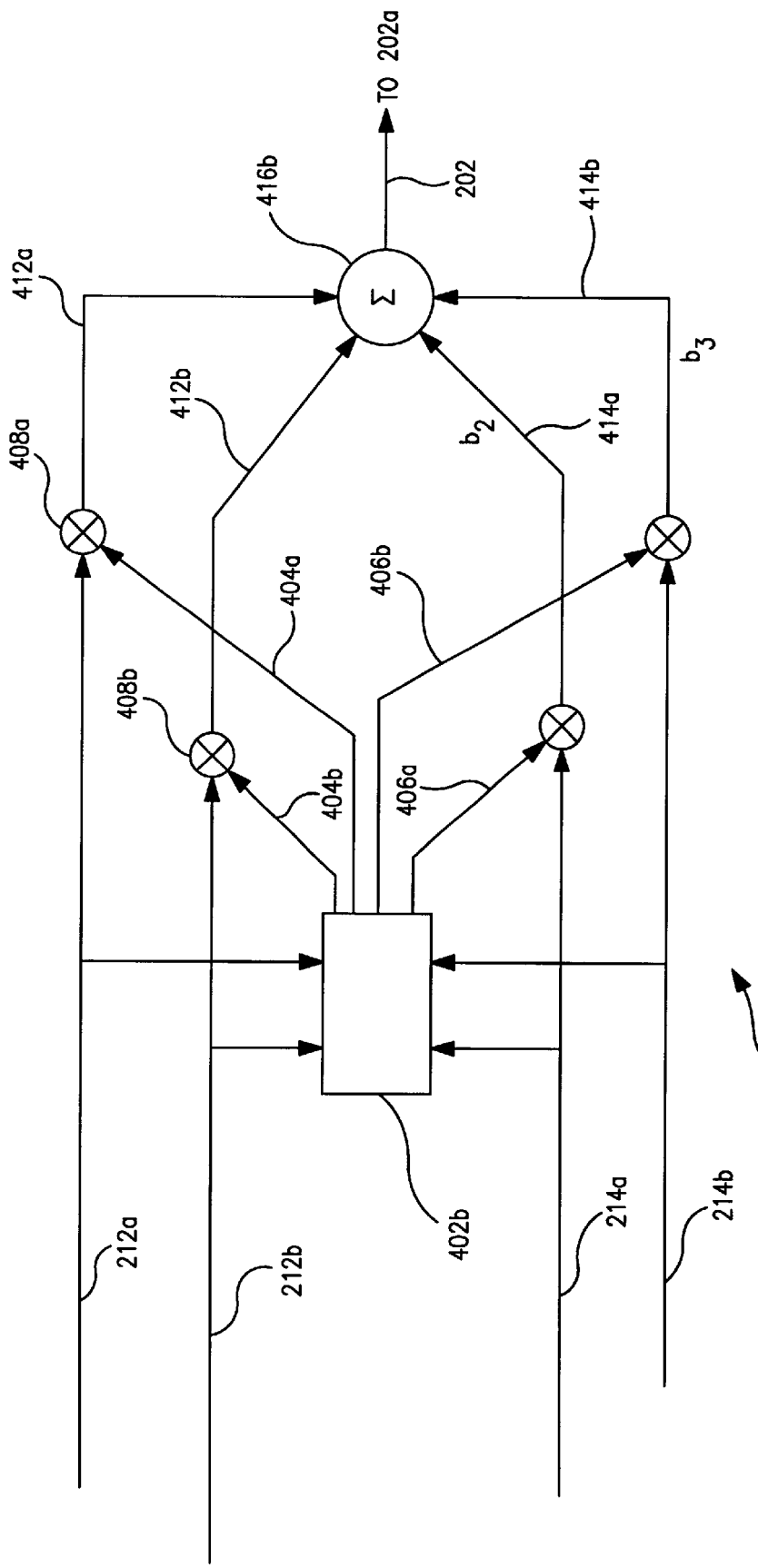
FIG. 11 is a third schematic block diagram of the weight coefficient generator of FIG. 4A.

The weight coefficient generator 400 of FIG. 4A is shown in greater detail in FIGS. 9–11. In FIG. 9, the weight coefficient generator 400 receives the resampled tissue signal 212 and the blood flow signal 214. The weight coefficient generator 400 includes a weight coefficient calculator 402 that calculates a set of coefficients ($b_0, b_1, b_2, \ldots b_n$) based upon one or more tissue imaging signals 212 and blood flow signals 214 and provides as output weighted signals 404, 406 indicative of the set of weight coefficients ($b_0, b_1, b_2, \ldots b_n$). Multipliers 408 and 410 multiply the tissue signal 212 and the blood flow signal 214 by the coefficients $b_1$ and $b_2$ providing thereby weighted tissue signal 412 and weighted blood flow signal 414. The weight coefficient generator 400 also includes an adder 416 that sums the weighted signals 412, 414. The output 202 of the weight coefficient generator 400 is a resolution cell 52.

Because the SAD technique utilizes resampling of the tissue signal 212, this method tends to degrade the spatial (axial) resolution of the tissue signal 212 as the window size, N, increases. Generally, the number of beamformed RF signals 116 used in Eq. (2) is two, which would be acceptable for a higher frame rate, but it will be recognized that a greater number of signals could be used for more temporal averaging and thus for a higher SNR. The subtraction operation performed by FIR filter 210b limits the number of taps in FIR filter 210b to two, thus making the filtering effect rather weak.

FIR (High-pass) Filter

Figure 4D:
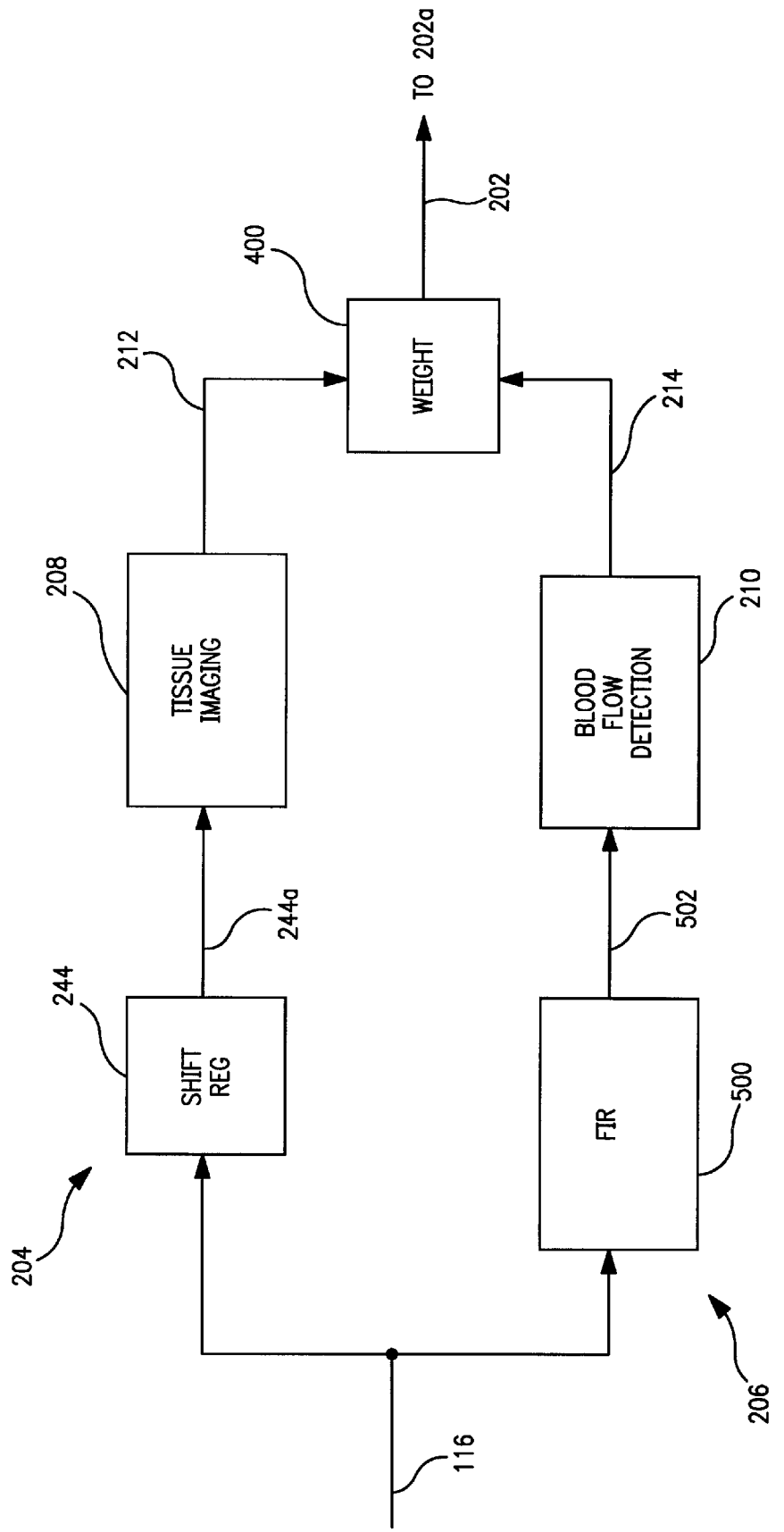
FIG. 4D is a schematic block diagram of an ultrasound beam processor having a temporal finite-impulse-response filter in the blood flow detection system.

To increase the filtering effects of the SAD calculator 210a, the number of terms in Eqn. 2 would need to increase. However, more than two taps would be needed in the FIR 210b and the SAD method of creating the blood flow signal 214 can no longer be used. Therefore, to increase the SNR for each resolution cell 52 in beam 50, while increasing the filtering effects in the blood flow detection, an M tap FIR filter 500 can be employed as seen in FIG. 4D.

Figure 4E:
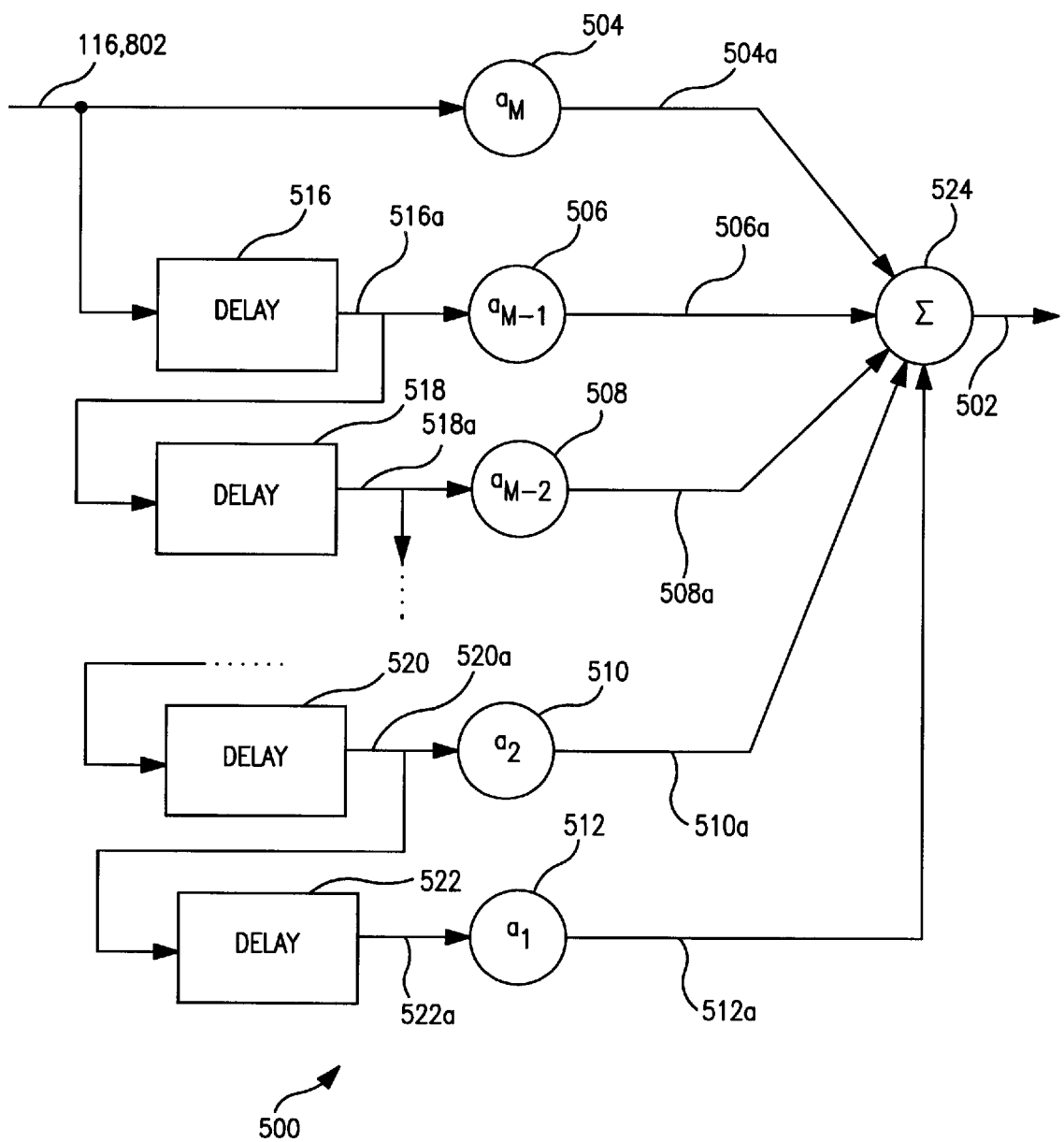
FIG. 4E is a schematic block diagram of the temporal finite-impulse-response filter of FIG. 4D.

The FIR filter 500 is shown in greater detail in FIG. 4E. In FIG. 4E, FIR filter 500 includes a number, M, of taps or branches. The output 502 of the FIR filter 500 can generally be expressed as follows:

$$Output = \sum_{j=1}^{M} a_j X_{i,j} \tag{3}$$

where $X_{ij}$ is a beamformed RF signal 116, i indicates the depth index of the beamformed RF signal 116, j indicates the time step at which the beamformed RF signal 116 was generated, M is the number of taps, or order, of the FIR filter 500 and $a_j$ are the filter coefficients. Filtering is performed on M pulse repetition frequency (PRF) based signals. Equation 3 represents the FIR filter method for a window 300 of size N=1 which results in a little smaller SNR. This filtering of M signals can be implemented in the configuration shown in FIG. 4E. In FIG. 4E, the line buffers 516, 518, 520, 522 store the data of the corresponding M transmissions of the RF beamformed signals 116.

Figure 12:
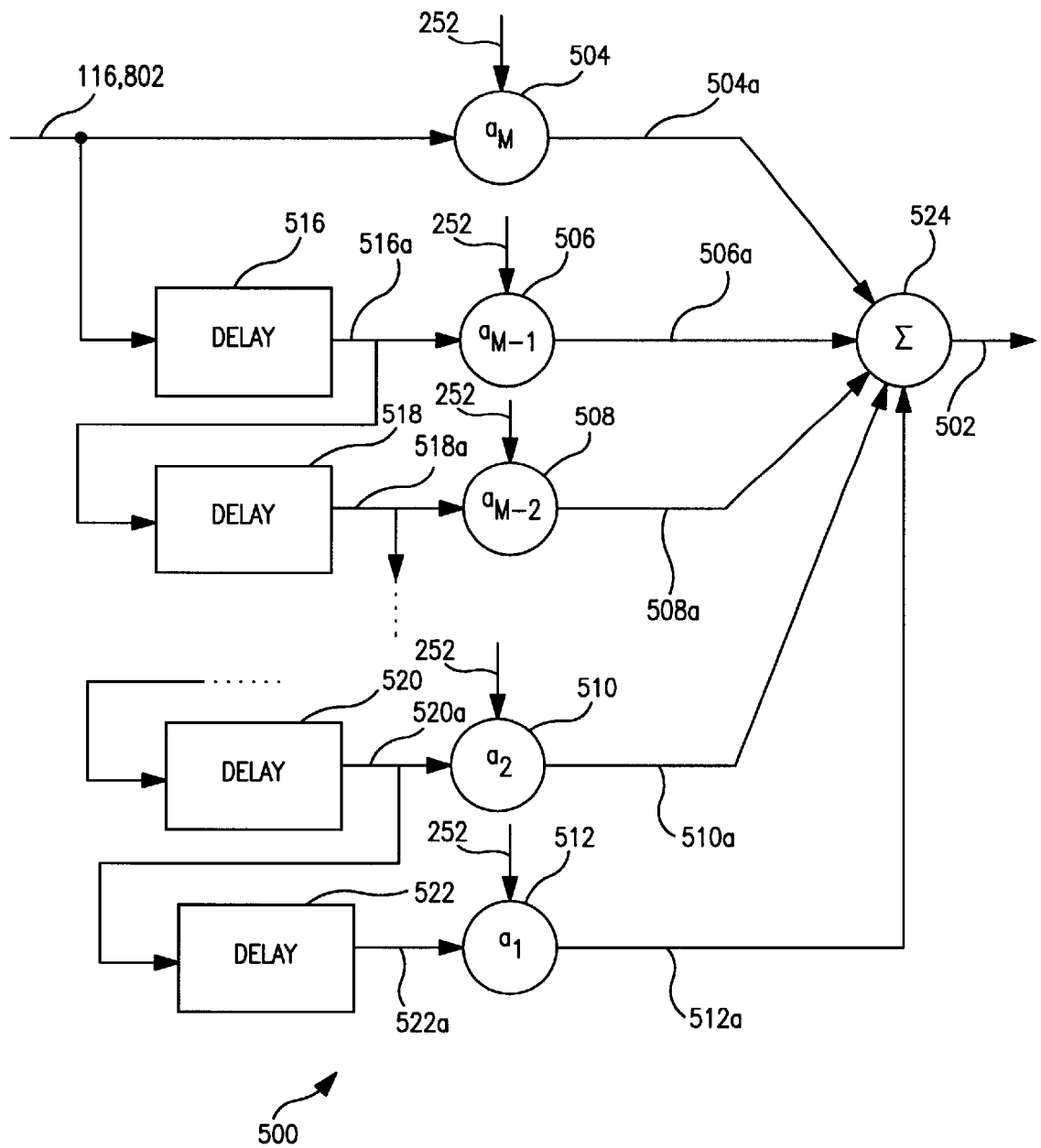
FIG. 12 is a schematic block diagram of the finite-impulse-response filter of FIG. 4D having adjustable filter coefficients.
Figure 13:
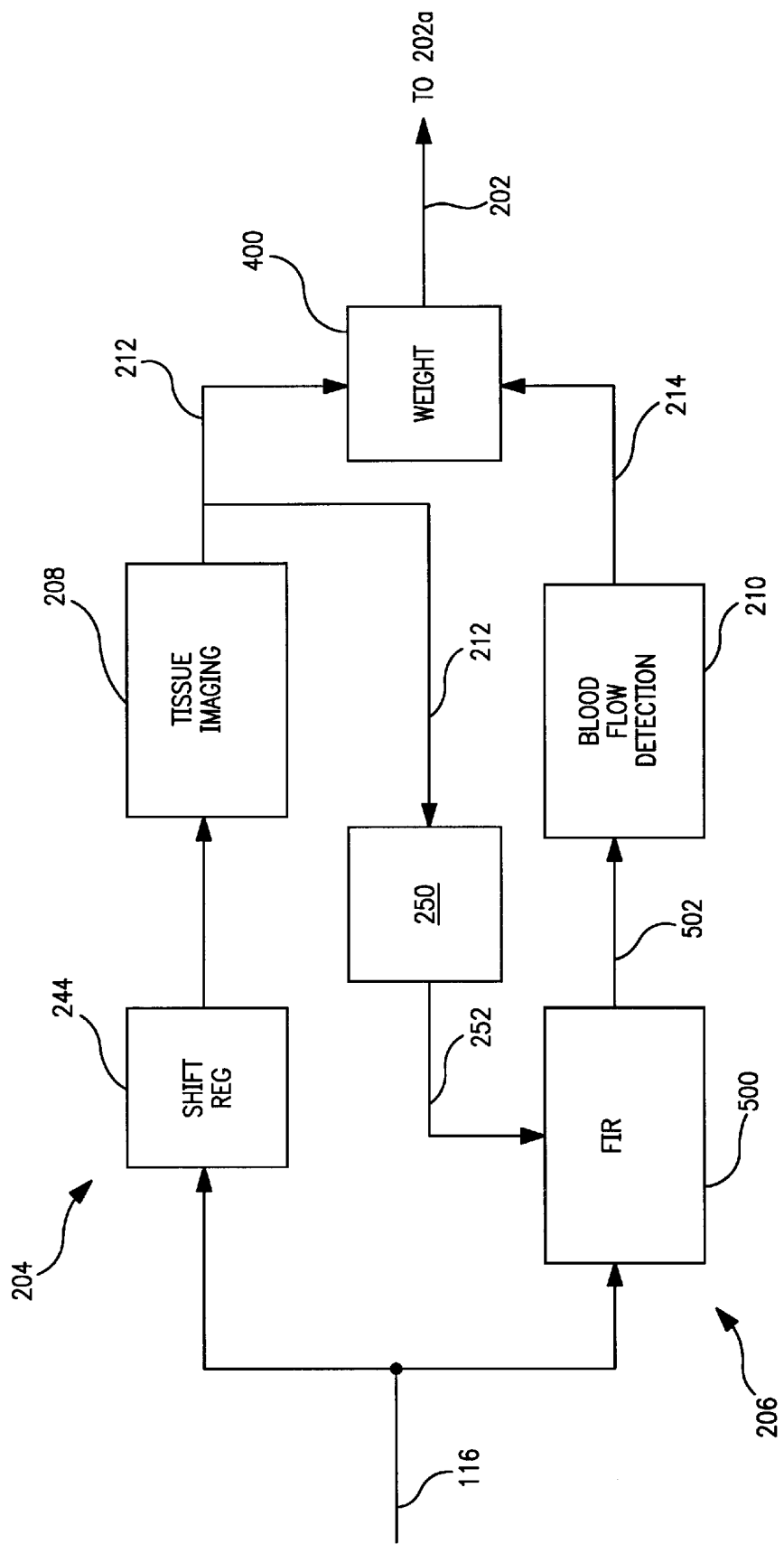
FIG. 13 is a schematic block diagram of an ultrasound beam processor having a finite-impulse-response filter in the blood flow detection system having adjustable filter coefficients.

Alternatively, for each of the taps of FIR 500, filtering effects can be adjusted to be stronger or weaker, depending on the magnitude and/or velocity of tissue signals 212. Such adjustment of the filtering can be accomplished as shown in FIGS. 12 and 13. In FIG. 12 the tissue imaging signal 212 is provided as input to a filter coefficient generator 250 for controlling the values of the filter coefficients, $a_j$, as seen in FIG. 13 at control signal 252.

The number of the filter taps, M, can be smaller than the number of transmissions, $M_x$, per beam direction. In this case, temporal averaging can be used to increase the SNR as follows:

$$Output = \sum_{k=1}^{M_x-M} \sum_{j=k}^{M+k-1} a_{j-k+1} X_{i,j} \tag{4}$$

As shown in FIG. 4D, after FIR filtering, the amplitude of the filter output 502 is detected at 210. However, as is also shown in FIG. 4B and FIG. 4D, a synchronizing device, such as a resampling device 220 and memory device, e.g., a shift register 244, is provided in the first signal branch 204. This is so because of the fact that the input 116 to the FIR filter 500 has been delayed by (M−1)×L increments where L is the number of signals per line. Thus, the input to the tissue imaging 208 in the first signal branch 204 must likewise be delayed (M−1)×L increments in order to synchronize the input to the tissue imaging 208 and the blood flow detection 210. Also, the number of signals is decreased by a factor of M and thus resampling 220 must account for this decrease. The shift register thus synchronizes the beamformed signal 116 with the filtered version thereof. It will be apparent to those skilled in the art that other methods of signal synchronization are possible, for example by timing of signals.

The blood flow signal 214 and the tissue signal 212 are provided as input to the weight coefficient generator 400. Weight coefficients ($b_0, b_1, b_2, \ldots b_n$) are determined by the weight coefficient calculator 402 as shown in FIG. 9. The amplitudes of the tissue signal 212 and the blood flow signal 214 are used to scale those signals 212, 214 by applying the appropriate weight coefficients at 404 and 406 respectively to the tissue and blood flow signals 212, 214 such that those signals 212, 214 would appear about equal in image brightness. For example, if the amplitudes of the tissue signal 212 and the blood flow signal 214 are $A_1$ and $A_2$, respectively the weight coefficients, $b_1$, $b_2$ can be chosen to satisfy the following equations:

$$\frac{A_1}{A_2} = \frac{b_2}{b_1} \tag{5}$$

or a ratio, $r_{12}$ can be introduced as follows:

$$\frac{A_1}{A_2} = r_{12} \frac{b_2}{b_1} \tag{6}$$

The weight coefficients $b_1$ and $b_2$, can be determined over a large area (i.e., an area larger than one resolution cell) to yield average values by using average amplitudes $A_1$ and $A_2$ over the area. The user can provide input data by adjusting the brightness of either the tissue signal 212 or blood flow signal 214 depending upon the user's preference or application. The aforesaid input data may be provided by a keyboard, a mouse a trackball or other such device.

Axial Averaging or Low-pass Filtering

Blood flow detection can be improved by increasing the window size, N. Axial averaging can be implemented by filtering according to the following equation:

$$Output = \sum_{i=1}^{N} \sum_{j=1}^{M} a_j X_{i,j} \quad (7)$$

A more general form of FIR low pass-filter, with filter coefficients, $c_i$, can replace the averaging as follows:

$$Output = \sum_{i=1}^{N} c_i \sum_{j=1}^{M} a_j X_{i,j} \quad (7a)$$

Figure 4F:
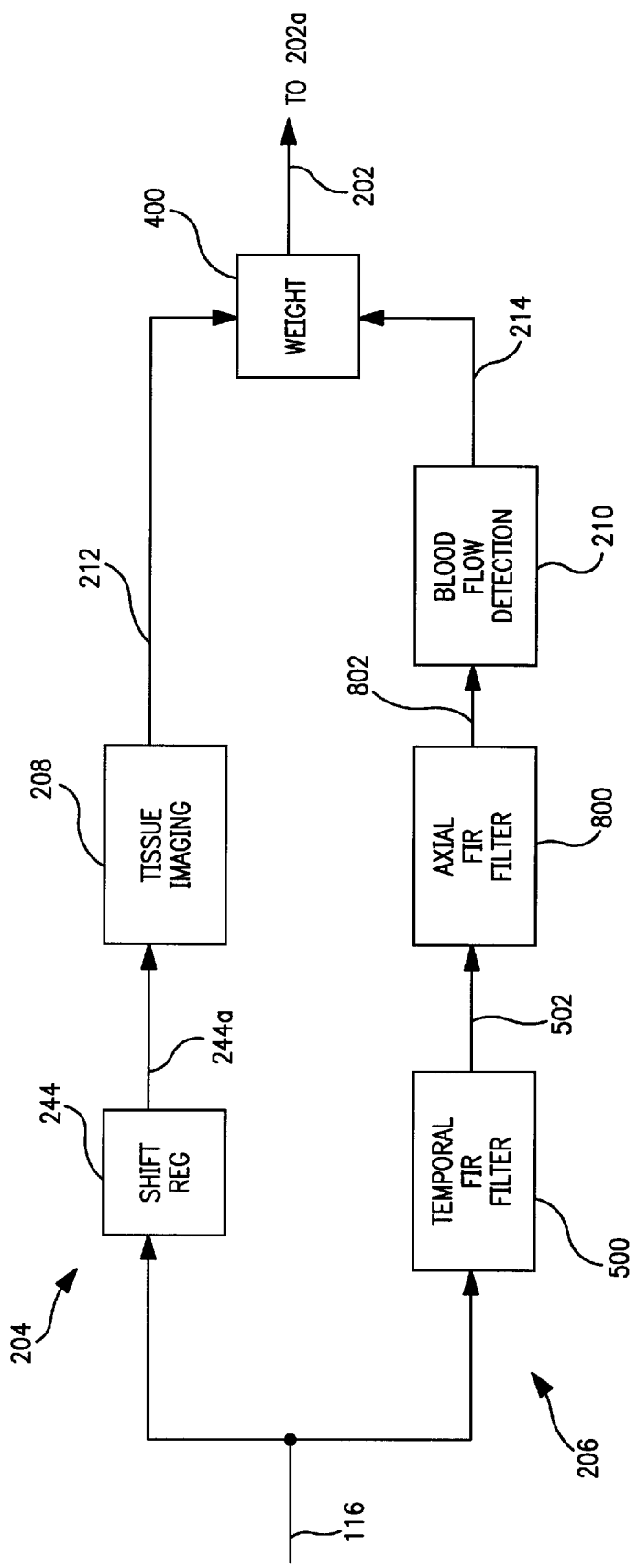
FIG. 4F is a schematic block diagram of an ultrasound beam processor having a first spatio-temporal filtering configuration in the blood flow detection system.
Figure 4G:
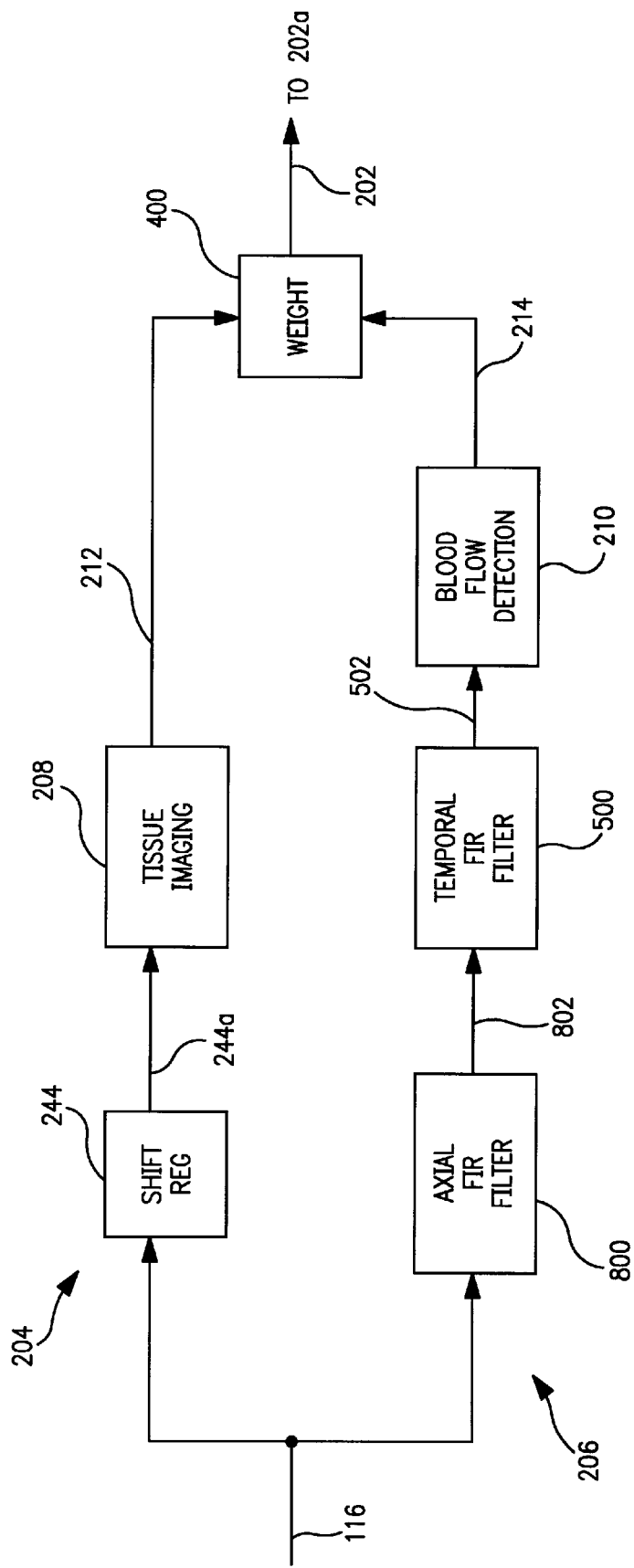
FIG. 4G is a schematic block diagram of an ultrasound beam processor having a second spatio-temporal filtering configuration in the blood flow detection system.
Figure 4H:
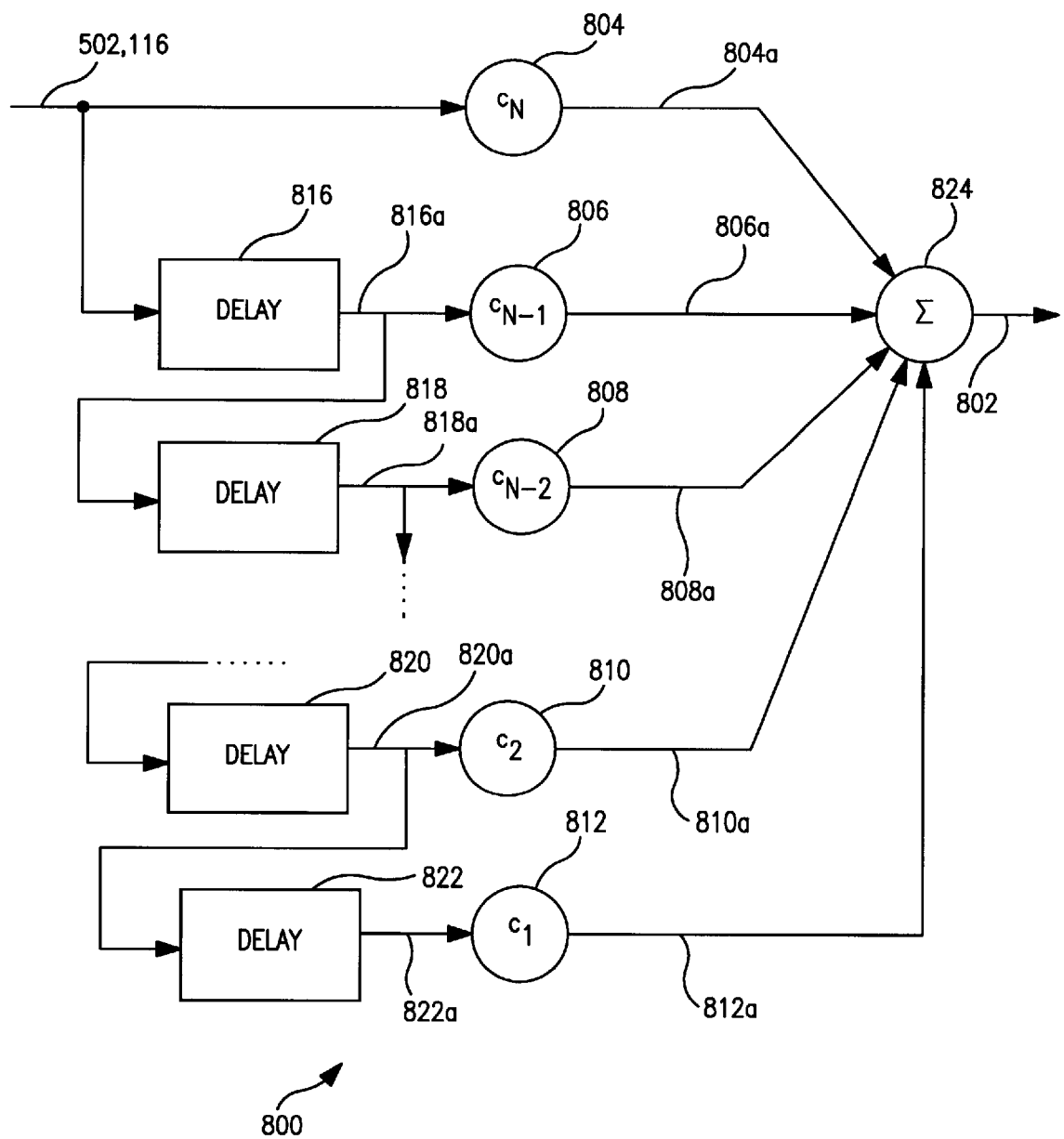
FIG. 4H is a schematic block diagram of a spatial finite-impulse-response filter of FIG. 4F.

If $M_x > M$ then,

Likewise, a more general FIR low-pass filter can replace the averaging as follows:

$$Output = \sum_{i=1}^{N} \sum_{k=1}^{Mx-M} \sum_{j=k}^{M+k-1} a_{j-k+1} X_{i,j} \quad (8)$$

$$Output = \sum_{i=1}^{N} c_i \sum_{k=1}^{Mx-M} \sum_{j=k}^{M+k-1} a_{j-k+1} X_{i,j} \quad (8a)$$

where $M_x$ is the number of transmissions per beam. This can be implemented by the configuration shown in FIG. 4F. In FIG. 4F, the second signal branch 206 is provided with a first FIR filter 500 and a second FIR filter 800. The first FIR filter 500 provides temporal filtering as described above, i.e., filtering over $M_x$ transmissions (FIG. 3). The second FIR filter 800, shown in FIG. 4H, provides filtering over the axial length of the beam 50 (FIG. 3). The shift register 244 of FIG. 4F now synchronizes the input to the tissue imaging 208 with the output 802 of the serial FIR filters 500, 800 for blood flow detection 210.

It will be recognized that the order in which the above spatio-temporal filtering 500, 800 is accomplished is immaterial. Thus, as seen in FIG. 4G, alternatively filtering over the axial length of the beam 50 (FIG. 3) can be performed on the beamformed RF signal 116 at 600 before temporal filtering over the $M_x$ transmissions (FIG. 3) as follows. If $M_x = M$ $$Output = \sum_{j=1}^{M} a_j \sum_{i=1}^{N} X_{i,j} \quad (9)$$

Again, an FIR low-pass filter can replace the simple averaging as follows:

$$Output = \sum_{j=1}^{M} a_j \sum_{i=1}^{N} c_i X_{i,j} \quad (9a)$$

if $M_x > M$; and for axial averaging (or $c_i = 1$)

$$Output = \sum_{k=1}^{Mx-M} \sum_{j=k}^{M+k-1} a_{j-k+1} \sum_{i=1}^{N} X_{i,j} \quad (10)$$

If an FIR low-pass filter is used to replace the averaging, then $$Output = \sum_{k=1}^{Mx-M} \sum_{j=k}^{M+k-1} a_{j-k+1} \sum_{i=1}^{N} c_i X_{i,j} \quad (10a)$$

This processing can be implemented by the configuration shown in FIG. 4G where the order of the filtering in FIG. 4F is reversed. The shift register 244 of FIG. 4G now synchronizes the input to the tissue imaging 208 with the output 502 of the serial FIR filters 600, 500 for blood flow detection 210. The tissue image signal 212 and the blood flow signal 214 of FIGS. 4F and 4G are provided to the weight coefficient generator 400 in the manner described above.

Both of the averaging methods, or FIR low-pass filtering, of FIGS. 4F and 4G increase the SNR but again at cost of spatial resolution. Also, the number of transmissions $M_x$ decreases the frame rate and thus cannot be too high. Therefore, it is an object of this invention to optimize the settings of axial averaging size, axial averaging method, the length of FIR filter (number of taps) so that blood flow is adequately detected while keeping good spatial and temporal resolutions.

Axial averaging (or FIR filtering), which affects axial resolution, can be balanced with the number of transmissions per beam or temporal averaging (or the number of FIR taps) while maintaining the same flow sensitivity. For example, the number of transmissions can be decreased while increasing the window size for axial averaging. This arrangement, for example, increases temporal resolution and is adequate for fast moving organs such as the heart. On the other hand, if an organ is stationary or slow moving, temporal averaging can be increased while decreasing the size of the axial averaging in order to maintain the same flow sensitivity or SNR.

Harmonic Imaging

Figure 5:
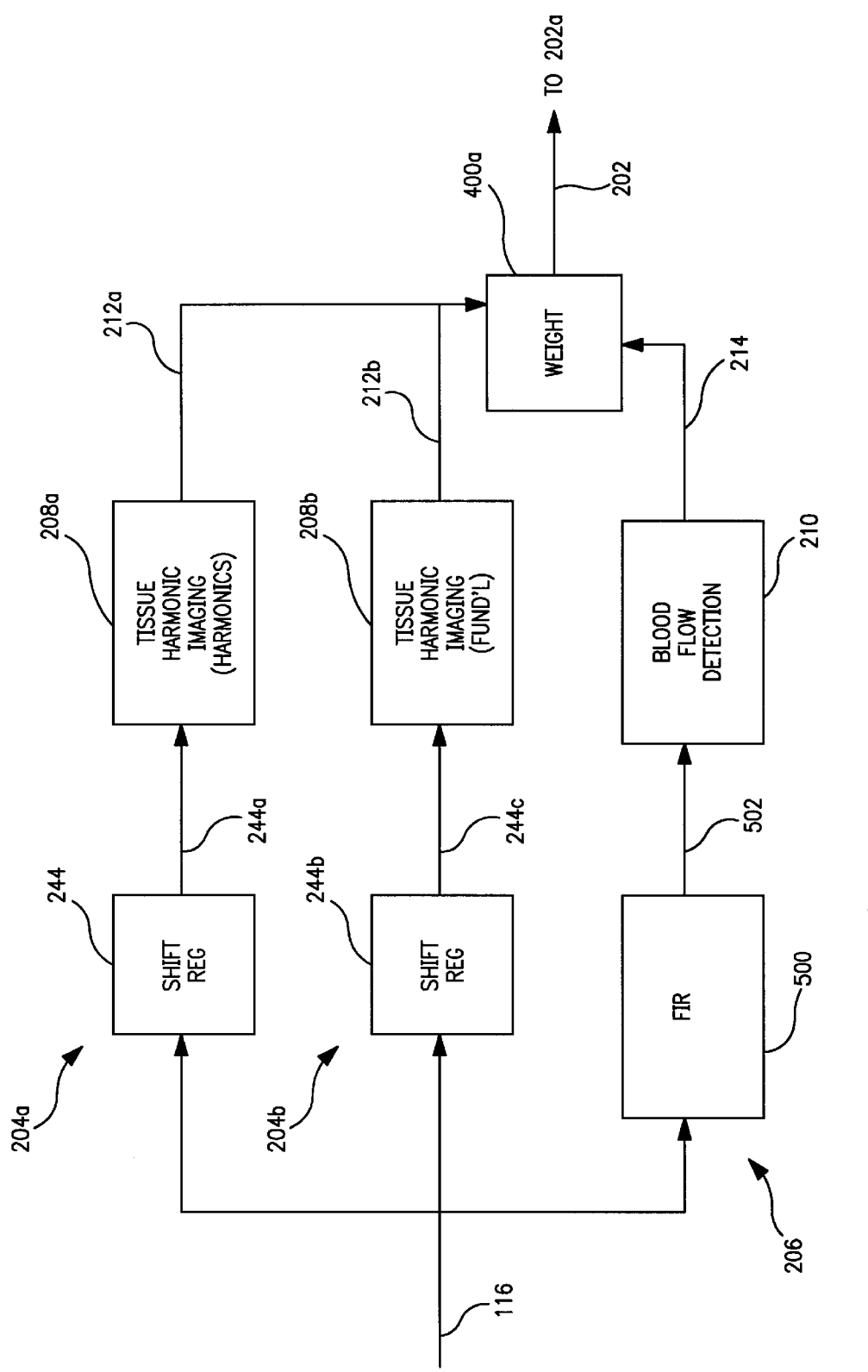
FIG. 5 is a schematic block diagram of an ultrasound beam processor including tissue harmonic imaging and a finite-impulse-response filter in the blood flow detection system.

Tissue imaging can be improved by using harmonics (eg., the $2^{nd}$, $3^{rd}$ or higher harmonics) which are at a frequency higher than the fundamental frequency. For example, harmonic imaging at twice the fundamental frequency can increase image quality due to higher spatial resolution, and also due to the presence of fewer artifacts or interference in the second harmonic signal than the signal at the fundamental frequency. This is due to the fact that harmonic frequencies are created along the wave propagation path rather than at the transmission source. FIG. 5 illustrates the block diagram of the harmonic imaging embodiment of the beam processor 200. The tissue imaging branch 204 now has two paths to process the beamformed RF signals 116, a first path 204b at the fundamental frequency and a second path 204a for higher harmonics. A fundamental image 212b and a harmonic image 212a are combined in the weight coefficient generator 400a to provide the appropriate weight coefficients to create an image having both the sharpness of harmonic imaging and the higher sensitivity of fundamental imaging. This weighting process is performed in the weight coefficient calculator 402a of FIG. 10. For example, if the amplitudes of the harmonic tissue signal 212a and the fundamental tissue signal 212b are $A_0$ and $A_1$ respectively, the weight coefficients, $b_0$, $b_1$ can be chosen to satisfy the following equation:

$$\frac{A_0}{A_1} = r_{01} \frac{b_1}{b_0} \quad (11)$$

where $r_{01}$ is a ratio. The sum of the weighted amplitudes of the tissue signals 412a, 412b can be made to equal the weighted amplitude of the blood flow signal 414 as follows:

$$A_0 b_0 + A_1 b_1 = A_2 b_2 \quad (12)$$

or a ratio r can be introduced as $$A_0 b_0 + A_1 b_1 = r A_2 b_2 \quad (13)$$

where $A_2$ is the amplitude of the blood flow signal 414. The user can also adjust the weight coefficients so as to adjust the quality of the tissue image signals 412a, 412b (e.g., sharpness, sensitivity, etc.) and the brightness of blood flow signal 414 with respect to that of the tissue image signals 412a, 412b. Adjusting the weight coefficients can be accomplished through the use of a keyboard, a mouse, a trackball or though other such devices.

Contrast Harmonic Imaging and Sub-harmonic Imaging

Figure 6:
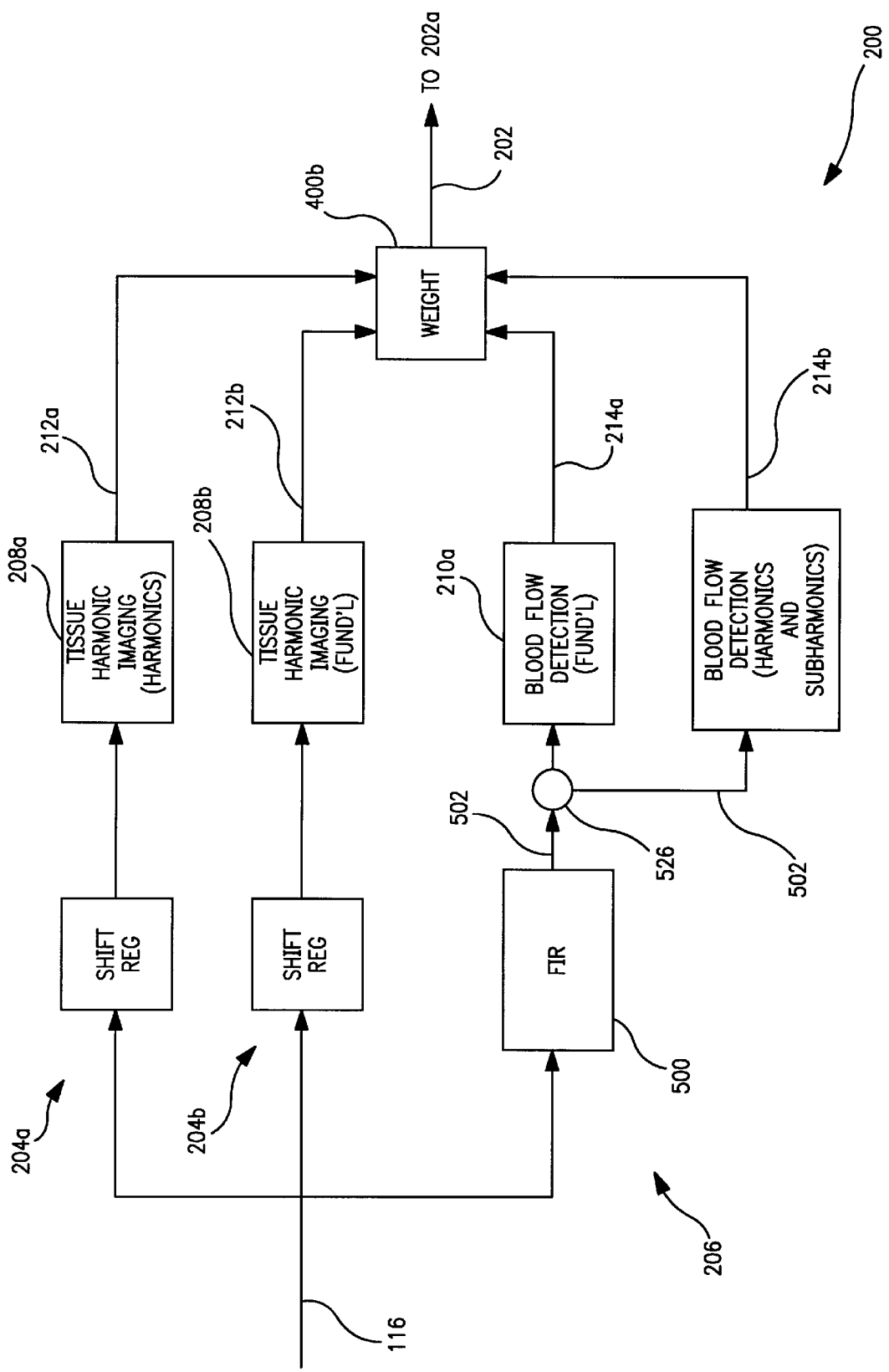
FIG. 6 is a schematic block diagram of an ultrasound beam processor including tissue harmonic imaging and contrast harmonic imaging in the blood flow detection system.

The use of ultrasound contrast agents can increase the blood flow signal 214. Thus, blood flow detection at harmonic frequencies, such as the $2^{nd}$ harmonic frequency, which is twice the fundamental frequency, is possible. Contrast agents are generally of encapsuled air bubbles that exhibit very high scattering properties. These contrast agents are injected into the blood flow to increase the scattered signal power by a factor of about 20–40 dB which makes harmonic blood flow detection possible. Contrast blood flow detection at harmonic frequencies has the advantage of containing less clutter than detection at the fundamental frequency. This can be achieved by the beam processor 200 shown in FIG. 6 and the weight coefficient generator 400b of FIG. 11. In this configuration, if contrast agents are not used, i.e., if contrast harmonic imaging is not employed, the harmonic blood flow signal 214b is not used and the appropriate weight coefficient 406b, is set equal to zero and a weighted fundamental blood flow signal 414a is used in the composite image 202. If contrast agents are used, weight coefficient 406a is set equal to zero and only a weighted harmonic blood flow signal 414b will be used in the composite image 202. Subharmonics, which are 1/S (where S=integer) of the fundamental frequency, and harmonic frequencies can be created by contrast agents and used as a blood flow signal 214b for the flow image and can be combined with the tissue image just like harmonics, which are integer multiples of the fundamental frequency.

Coded Transmission

Figure 7:
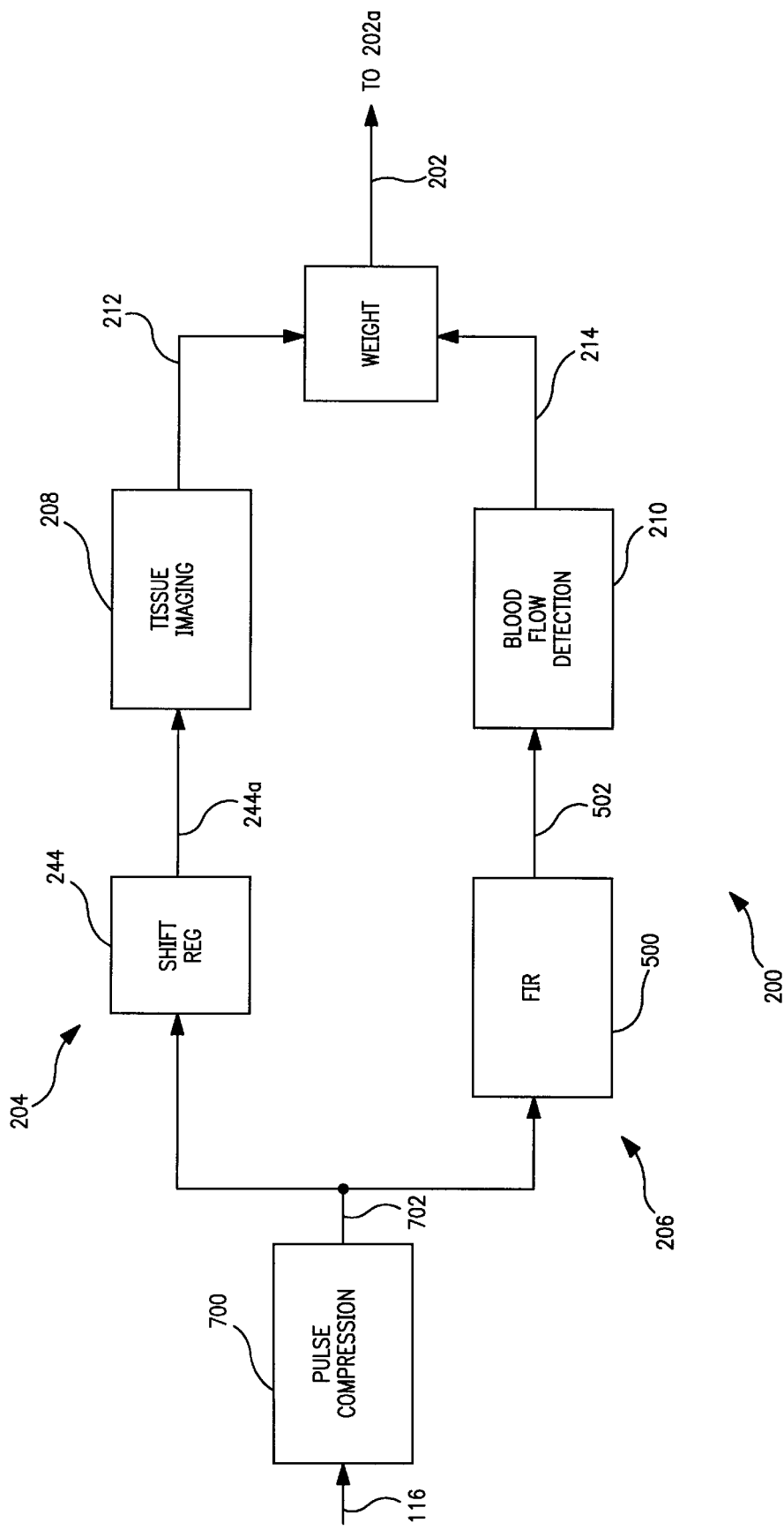
FIG. 7 is a schematic block diagram of an ultrasound beam processor including pulse compression filter and a finite-impulse-response filter in the blood flow detection system.

Coded transmission can further increase the signal amplitude and SNR by transmitting a waveform at the amplitude of the regular transmission method but of a longer pulse duration. The instantaneous power in the coded transmission is the same as in the regular transmission. However, the coded transmission method transmits more energy by transmitting a longer ultrasound waveform. Upon reception, the coded transmission method compresses the beamformed RF signal 116 by a pulse compression filter 700. This method can be implemented by the configuration shown in FIG. 7. The pulse compression filter 700 is applied to the beamformed RF signal 116 whereby the beamformed RF signal 116 is compressed in time, resulting in more power and a higher SNR. Therefore, using the coded transmission method, blood flow detection 210 is further enhanced. In the preferred embodiment, the pulse compression filter 700 is used as shown in FIG. 7 so that only one pulse compression filter 700 is necessary. After the pulse compression filter 700 is applied, the blood flow is detected as described above with respect to FIG. 4D but with a higher resultant SNR. The coded transmission waveform can be of Barker, Golay, or Chirp signals or other wave forms.

DSP Based Beam Processor

Figure 8:
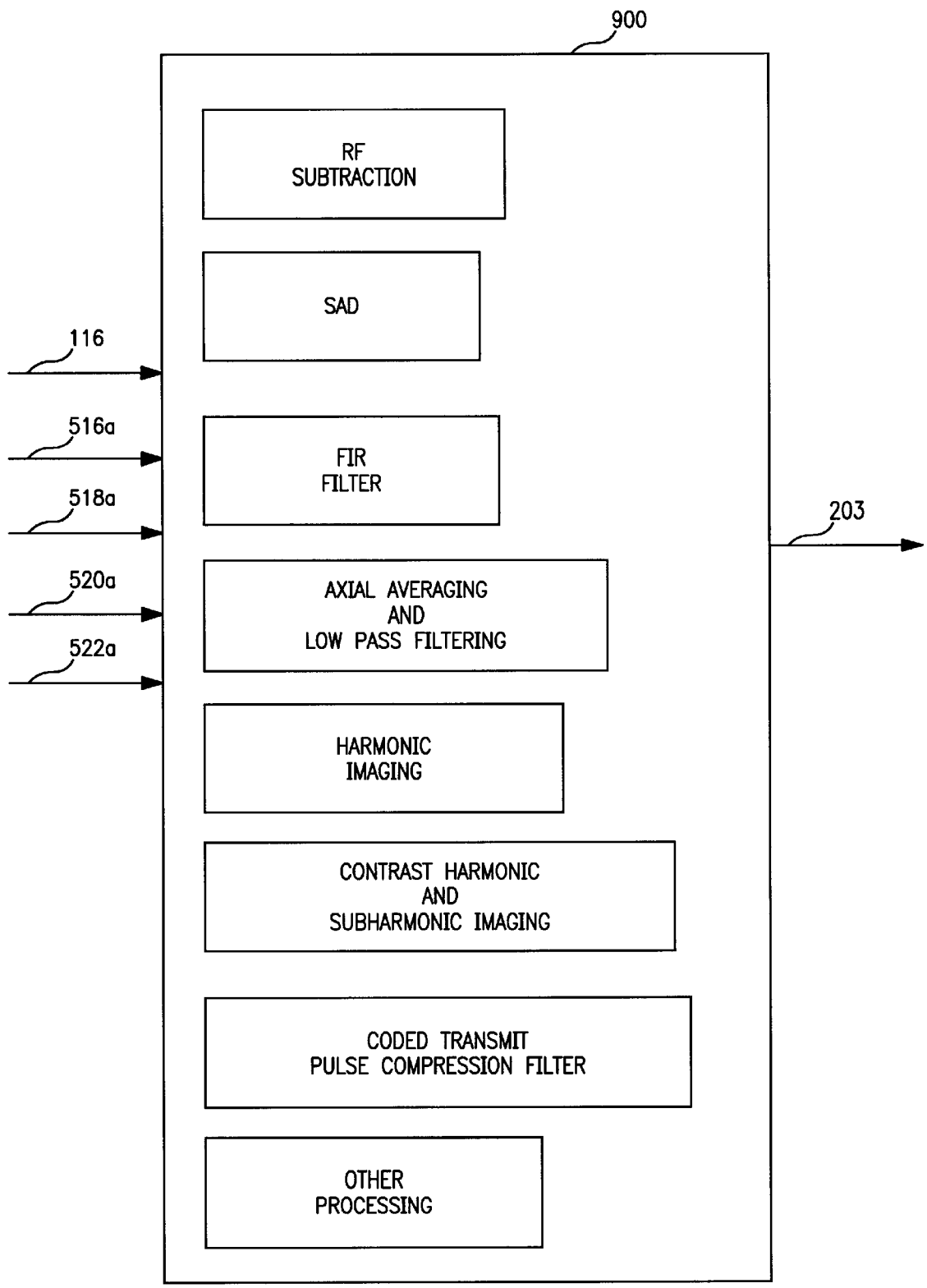
FIG. 8 is a schematic block diagram of a digital signal processing based ultrasound beam processor.

The SAD method, which was previously described, requires a calculation of an absolute value as well as a subtraction or FIR filtering. The axial averaging also requires FIR filters or a running average calculator in the beam, or axial direction. All of the above processing can be individually achieved by discrete electronic components. However, the methods described above can be easily implemented by a digital signal processor based beam processor as shown in FIG. 8. The DSP can be programmed to perform various forms of blood flow detection as well as averaging methods and thus is well suited for this type of operation that may require various lengths or forms of averaging. DSPs can be, for example, TigerSharc DSPs, Analog Devices Inc. or Texas Instrument's DSPs for example, TMS1380C6201.

Image Display

The output signal 203 in FIGS. 4 through 8 is converted to either a color or grayscale image by a look-up table (not shown) and the digital scan converter (DSC) 126.

The disclosed invention may be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

It will be understood that those skilled in the art may conceive variations and modifications to the preferred embodiment shown herein within the scope and intent of the claims. While the present invention has been described as carried out in a specific embodiment thereof, it is not intended to be limited thereby but is intended to cover the invention broadly within the scope and spirit of the claims.

What is claimed is:

1. A method of blood flow imaging comprising:
   receiving a beamformed signal indicative of an ultrasound signal reflected from a target within a body;
   responsive to the beamformed signal, imaging tissue within the body, generating thereby a tissue signal;
   responsive to the beamformed signal, detecting blood flow within the body, generating thereby a blood flow signal; and
   combining the tissue signal and the blood flow signal generating thereby a composite image of tissue and blood flow within the body.

2. The method as set for in claim 1 wherein detecting blood flow within the body comprises analyzing the difference between the beamformed signal and a delayed or displaced version thereof.

3. The method as set for in claim 2 further comprising synchronizing and resampling the beamformed signal with the delayed or displaced version thereof.

4. The method as set for in claim 2 wherein analyzing the difference between the beamformed signal and a delayed or displaced version thereof comprises calculating a sum of absolute differences of the beamformed signal and a delayed or displaced version thereof.

5. The method as set for in claim 1 further comprising:
filtering the beamformed signal generating thereby a filtered beam formed signal indicative of an ultrasound signal reflected from a target within the body; and
synchronizing the beamformed signal with the filtered version thereof.

6. The method as set for in claim 5 wherein synchronizing the beamformed signal with the filtered version thereof includes applying the beamformed signal to a resampling and memory device operative to retain the beamformed signal for a prescribed time interval.

7. The method as set for in claim 5 wherein filtering the beamformed signal comprises temporally filtering the beamformed signal.

8. The method as set for in claim 5 wherein filtering the beamformed signal comprises spatio-temporally filtering the beamformed signal.

9. The method as set for in claim 5 wherein imaging tissue within the body comprises tissue harmonic imaging the beamformed signal.

10. The method as set forth in claim 9 wherein tissue harmonic imaging comprises tissue harmonic imaging at a harmonic frequency of the beamformed signal generating thereby a harmonic tissue image.

11. The method as set forth in claim 9 wherein tissue harmonic imaging comprises tissue harmonic imaging at the fundamental frequency of the beamformed signal generating thereby a fundamental tissue image.

12. The method as set for in claim 5 wherein detecting blood flow within the body comprises detecting the component of the filtered beamformed signal at the fundamental frequency thereof.

13. The method as set for in claim 5 wherein detecting blood flow within the body comprises detecting the component of the filtered beamformed signal at a harmonic frequency thereof.

14. The method as set for in claim 5 further comprising compressing the beamformed signal.

15. The method as set for in claim 1 wherein combining the tissue signal and the blood flow signal comprises:
generating at least one weight coefficient;
multiplying a first weight coefficient thereof by the tissue signal generating thereby a weighted tissue signal;
multiplying a second weight coefficient thereof by the blood flow signal generating thereby a weighted blood flow signal; and
summing the weighted tissue signal and the weighted blood flow signal generating thereby the composite image of tissue and blood flow.

16. The method as set for in claim 12 wherein combining the tissue signal and the blood flow signal comprises:
generating at least one weight coefficient;
multiplying a first weight coefficient thereof by the harmonic tissue image generating thereby a weighted component of the harmonic tissue image at a harmonic frequency thereof;
multiplying a second weight coefficient thereof by the fundamental tissue image generating thereby a weighted component of the fundamental tissue image at the fundamental frequency thereof;
multiplying a third weight coefficient by the blood flow signal generating thereby a weighted blood flow signal; and
summing the weighted component of the harmonic tissue image at a harmonic frequency thereof, the weighted component of the fundamental tissue image at the fundamental frequency thereof and the weighted blood flow signal generating thereby the composite image of tissue and blood flow.

17. The method as set for in claim 16 further comprising:
multiplying a third weight coefficient by the component of the temporally filtered beamformed signal at the fundamental frequency thereof generating thereby a weighted fundamental component of the temporally filtered beamformed signal;
multiplying a fourth weight coefficient by the component of the temporally filtered beamformed signal at a harmonic or subharmonic frequency thereof generating thereby a weighted harmonic or subharmonic component of the temporally filtered beamformed signal; and
summing the weighted fundamental component of the temporally filtered beamformed signal and the weighted harmonic or subharmonic frequency of the component of the temporally filtered beamformed signal.

18. The method as set forth in claim 1 further comprising converting the composite image to a color or grayscale image.

19. A storage medium encoded with a machine-readable computer program code for processing a beamformed signal indicative of an ultrasound signal reflected from a target within a body, the storage medium including instructions for causing a beam processor to implement a method of blood flow imaging comprising:
receiving the beamformed signal;
responsive to the beamformed signal, imaging tissue within the body, generating thereby a tissue signal;
responsive to the beamformed signal, detecting blood flow within the body, generating thereby a blood flow signal; and
combining the tissue signal and the blood flow signal generating thereby a composite image of tissue and blood flow within the body.

20. The storage medium as set forth in claim 19 wherein detecting blood flow within the body comprises analyzing the difference between the beamformed signal and a delayed or displaced version thereof.

21. The storage medium as set for in claim 20 further comprising synchronizing and resampling the beamformed signal with the delayed or displaced version thereof.

22. The storage medium as set for in claim 20 wherein analyzing the difference between the beamformed signal and a delayed or displaced version thereof comprises calculating a sum of absolute differences of the beamformed signal and a delayed or displaced version thereof.

23. The storage medium as set for in claim 19 further comprising:
filtering the beamformed signal generating thereby a filtered beam formed signal indicative of an ultrasound signal reflected from a target within the body; and
synchronizing the beamformed signal with the filtered version thereof.

24. The storage medium as set for in claim 23 wherein synchronizing the beamformed signal with the filtered version thereof includes applying the beamformed signal to a resampling and memory device operative to retain the beamformed signal for a prescribed time interval.

25. The storage medium as set for in claim 23 wherein filtering the beamformed signal comprises temporally filtering the beamformed signal.

26. The storage medium as set for in claim 23 wherein filtering the beamformed signal comprises spatio-temporally filtering the beamformed signal.

27. The storage medium as set for in claim 23 wherein imaging tissue within the body comprises tissue harmonic imaging the beamformed signal.

28. The storage medium as set forth in claim 27 wherein tissue harmonic imaging comprises tissue harmonic imaging at a harmonic frequency of the beamformed signal generating thereby a harmonic tissue image.

29. The storage medium as set forth in claim 27 wherein tissue harmonic imaging comprises tissue harmonic imaging at the fundamental frequency of the beamformed signal generating thereby a fundamental tissue image.

30. The storage medium as set for in claim 23 wherein detecting blood flow within the body comprises detecting the component of the filtered beamformed signal at the fundamental frequency thereof.

31. The storage medium as set for in claim 23 wherein detecting blood flow within the body comprises detecting the component of the filtered beamformed signal at a harmonic frequency thereof.

32. The storage medium as set for in claim 23 further comprising compressing the beamformed signal.

33. The storage medium as set for in claim 19 wherein combining the tissue signal and the blood flow signal comprises:
  generating at least one weight coefficient;
  multiplying a first weight coefficient thereof by the tissue signal generating thereby a weighted tissue signal;
  multiplying a second weight coefficient thereof by the blood flow signal generating thereby a weighted blood flow signal; and
  summing the weighted tissue signal and the weighted blood flow signal generating thereby the composite image of tissue and blood flow.

34. The storage medium as set for in claim 30 wherein combining the tissue signal and the blood flow signal comprises:
  generating at least one weight coefficient;
  multiplying a first weight coefficient thereof by the harmonic tissue image generating thereby a weighted component of the harmonic tissue image at a harmonic frequency thereof;
  multiplying a second weight coefficient thereof by the fundamental tissue image generating thereby a weighted component of the fundamental tissue image at the fundamental frequency thereof;
  multiplying a third weight coefficient by the blood flow signal generating thereby a weighted blood flow signal; and
  summing the weighted component of the harmonic tissue image at a harmonic frequency thereof, the weighted component of the fundamental tissue image at the fundamental frequency thereof and the weighted blood flow signal generating thereby the composite image of tissue and blood flow.

35. The storage medium as set for in claim 34 further comprising:
  multiplying a third weight coefficient by the component of the temporally filtered beamformed signal at the fundamental frequency thereof generating thereby a weighted fundamental component of the temporally filtered beamformed signal;
  multiplying a fourth weight coefficient by the component of the temporally filtered beamformed signal at a harmonic or subharmonic frequency thereof generating thereby a weighted harmonic or subharmonic component of the temporally filtered beamformed signal; and
  summing the weighted fundamental component of the temporally filtered beamformed signal and the weighted harmonic or subharmonic frequency of the component of the temporally filtered beamformed signal.

36. The storage medium as set forth in claim 19 further comprising converting the composite image to a color or grayscale image.

37. A beam processor for blood flow imaging comprising:
  a tissue imaging system receiving a beamformed signal indicative of an ultrasound signal reflected from a target within a body generating thereby a tissue signal;
  a blood flow detection system receiving the beam formed signal generating thereby a blood flow signal; and
  a weight coefficient generator for combining the tissue signal and the blood flow signal generating thereby a composite image of tissue and blood flow within the body.

38. The beam processor as set for in claim 37 wherein the blood flow detection system comprises a system for analyzing the difference between the beamformed signal and a delayed or displaced version thereof.

39. The beam processor as set for in claim 38 further comprising a system for synchronizing the beamformed signal with the delayed or displaced version thereof.

40. The beam processor as set for in claim 38 wherein the system for analyzing the difference between the beamformed signal and a delayed or displaced version thereof comprises a system for calculating a sum of absolute differences of the beamformed signal and a delayed or displaced version thereof.

41. The beam processor as set for in claim 37 further comprising:
  a filter for filtering the beamformed signal generating thereby a filtered beamformed signal indicative of an ultrasound signal reflected from a target within the body; and
  a synchronizer for synchronizing the beamformed signal with the filtered version thereof.

42. The beam processor as set for in claim 41 wherein the synchronizer includes a resampling and memory device operative to retain the beamformed signal for a prescribed time interval.

43. The beam processor as set for in claim 41 wherein the filter for filtering the beamformed signal comprises a temporal filter.

44. The beam processor as set for in claim 41 wherein the filter comprises a spatio-temporal filter.

45. The beam processor as set for in claim 41 wherein the tissue imaging system comprises a tissue harmonic imaging system.

46. The beam processor as set forth in claim 45 wherein the tissue harmonic imaging system comprises a tissue harmonic imaging system for imaging at a harmonic frequency of the beamformed signal generating thereby a harmonic tissue image.

47. The beam processor as set forth in claim 45 wherein the tissue harmonic imaging system comprises a tissue harmonic imaging system for imaging at the fundamental frequency of the beamformed signal generating thereby a fundamental tissue image.

48. The beam processor as set for in claim 41 wherein the blood flow detection system comprises a blood flow detection system for detecting the component of the filtered beamformed signal at the fundamental frequency thereof.

49. The beam processor as set for in claim 41 wherein blood flow detection system comprises a blood flow detection system for detecting the component of the filtered beamformed signal at a harmonic or subharmonic frequency thereof.

50. The beam processor as set for in claim 41 further comprising a pulse compression filter for compressing the beamformed signal.

51. The method as set forth in claim 5 further comprising adjusting the filtering of the beamformed signal in response to the tissue signal.

52. The storage medium as set forth in claim 23 further comprising adjusting the filtering of the beamformed signal in response to the tissue signal.

53. The beam processor as set forth in claim 43 further comprising a controller for receiving the tissue signal and responsive thereto for providing as output a control signal for controlling the filtering of the beamformed signal.

* * * * *

UNITED STATES PATENT AND TRADEMARK OFFICE
CERTIFICATE OF CORRECTION

PATENT NO. : 6,599,248 B1
DATED : July 29, 2003
INVENTOR(S) : Tadashi Tamura

It is certified that error appears in the above-identified patent and that said Letters Patent is hereby corrected as shown below:

<u>Title page,</u>
Item [73], Assignee, change "Aloka, Wallingford, CT (US)" to read -- Aloka Co., Ltd. (JP) --.

Signed and Sealed this

Twenty-fifth Day of October, 2005

JON W. DUDAS
*Director of the United States Patent and Trademark Office*